United States Patent
Kai et al.

(10) Patent No.: US 12,103,163 B2
(45) Date of Patent: Oct. 1, 2024

(54) CONTROL APPARATUS AND CONTROL METHOD

(71) Applicant: SONY GROUP CORPORATION, Tokyo (JP)

(72) Inventors: Toshimitsu Kai, Tokyo (JP); Kazuo Hongo, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 453 days.

(21) Appl. No.: 17/310,041

(22) PCT Filed: Dec. 10, 2019

(86) PCT No.: PCT/JP2019/048182
§ 371 (c)(1),
(2) Date: Jul. 13, 2021

(87) PCT Pub. No.: WO2020/153020
PCT Pub. Date: Jul. 30, 2020

(65) Prior Publication Data
US 2022/0088794 A1    Mar. 24, 2022

(30) Foreign Application Priority Data

Jan. 22, 2019    (JP) ................................. 2019-008409

(51) Int. Cl.
*B25J 13/08*    (2006.01)
*B25J 15/00*    (2006.01)
*G01N 33/02*    (2006.01)

(52) U.S. Cl.
CPC ......... *B25J 13/087* (2013.01); *B25J 15/0033* (2013.01); *G01N 33/02* (2013.01)

(58) Field of Classification Search
CPC .... B25J 13/087; B25J 15/0033; B25J 9/1612; B25J 9/1694; B25J 11/0045; B25J 15/10; G01N 33/02
See application file for complete search history.

(56) References Cited

U.S. PATENT DOCUMENTS 6,374,662 B1    4/2002 Oda et al.
2005/0252273 A1*  11/2005 Imoto ................ G01N 33/0009
                                                    73/23.2
(Continued)

FOREIGN PATENT DOCUMENTS

AU    2003242433 A1    12/2003
AU    2015311234 A1    2/2017
(Continued)

OTHER PUBLICATIONS

International Search Report and Written Opinion of PCT Application No. PCT/JP2019/048182, issued on Mar. 3, 2020, 11 pages of ISRWO.

*Primary Examiner* — Adam R Mott
*Assistant Examiner* — Alyzia N Dilworth
(74) *Attorney, Agent, or Firm* — CHIP LAW GROUP

(57) ABSTRACT

A control apparatus includes a determining section that determines freshness of a target object on the basis of odor data of the target object sensed by an odor sensor, and an operation control section that performs control such that operation predefined for the target object is executed on the basis of the freshness is provided.

18 Claims, 11 Drawing Sheets

(56) References Cited

U.S. PATENT DOCUMENTS

| | | | |
|---|---|---|---|
| 2016/0059412 A1* | 3/2016 | Oleynik | B25J 19/02 |
| | | | 700/250 |
| 2018/0279023 A1* | 9/2018 | Taylor | H04Q 9/00 |
| 2018/0285894 A1 | 10/2018 | Kankainen et al. | |
| 2018/0374144 A1 | 12/2018 | Smilowitz et al. | |
| 2019/0056370 A1* | 2/2019 | Yamasaki | G01N 29/022 |
| 2019/0261565 A1 | 8/2019 | Robertson et al. | |
| 2019/0261566 A1 | 8/2019 | Robertson et al. | |

FOREIGN PATENT DOCUMENTS

| | | |
|---|---|---|
| AU | 2017357645 A1 | 5/2019 |
| CA | 2959698 A1 | 3/2016 |
| CN | 107343382 A | 11/2017 |
| CN | 107877537 A | 4/2018 |
| CN | 108520593 A | 9/2018 |
| CN | 110139552 A | 8/2019 |
| EP | 3188625 A1 | 7/2017 |
| EP | 3537867 A1 | 9/2019 |
| JP | 05-131387 A | 5/1993 |
| JP | 08-81052 A | 3/1996 |
| JP | 2004-053582 A | 2/2004 |
| JP | 2005-147793 A | 6/2005 |
| JP | 2006-341957 A | 12/2006 |
| JP | 2015-003284 A | 1/2015 |
| JP | 2017-536247 A | 12/2017 |
| KR | 10-2006-0132348 A | 12/2006 |
| KR | 10-2017-0061686 A | 6/2017 |
| RU | 2017106935 A | 9/2018 |
| SG | 11201701093 S | 3/2017 |
| WO | 2003/106975 A1 | 12/2003 |
| WO | 2016/034269 A1 | 3/2016 |
| WO | 2017/051070 A1 | 3/2017 |
| WO | 2017/176717 A1 | 10/2017 |
| WO | 2018/087546 A1 | 5/2018 |

* cited by examiner

CONTROL APPARATUS AND CONTROL METHOD

CROSS REFERENCE TO RELATED APPLICATIONS

This application is a U.S. National Phase of International Patent Application No. PCT/JP2019/048182 filed on Dec. 10, 2019, which claims priority benefit of Japanese Patent Application No. JP 2019-008409 filed in the Japan Patent Office on Jan. 22, 2019. Each of the above-referenced applications is hereby incorporated herein by reference in its entirety.

TECHNICAL FIELD

The present disclosure relates to a control apparatus, a control method, and a program.

BACKGROUND ART

In recent years, there are known technologies for managing target objects. For example, there is a disclosed technology in which IC tag information of target objects is read out from IC (Integrated Circuit) tags attached to the target objects, and the target objects are moved to predetermined locations on the basis of the IC tag information having been read out (see PTL 1, for example). In addition, there is a disclosed technology in which the shapes of target objects are recognized by image recognition, and the target objects are sorted out on the basis of the recognized shapes (see PTL 2, for example).

CITATION LIST

Patent Literature

[PTL 1]
JP-2006-341957-.
[PTL 2]
JP-H8-81052-A

SUMMARY

Technical Problem

However, it is desired to provide a technology for more highly precisely executing operation suited for target objects.

Solution to Problem

According to the present disclosure, a control apparatus including a determining section that determines freshness of a target object on a basis of odor data of the target object sensed by an odor sensor, and an operation control section that performs control such that operation predefined for the target object is executed on the basis of the freshness is provided.

According to the present disclosure, a control method including determining freshness of a target object on the basis of odor data of the target object sensed by an odor sensor, and performing, by a processor, control such that operation predefined for the target object is executed on the basis of the freshness is provided.

According to the present disclosure, a program for causing a computer to function as a control apparatus including a determining section that determines freshness of a target object on the basis of odor data of the target object sensed by an odor sensor, and an operation control section that performs control such that operation predefined for the target object is executed on the basis of the freshness is provided.

DESCRIPTION OF EMBODIMENTS

Figure 1:
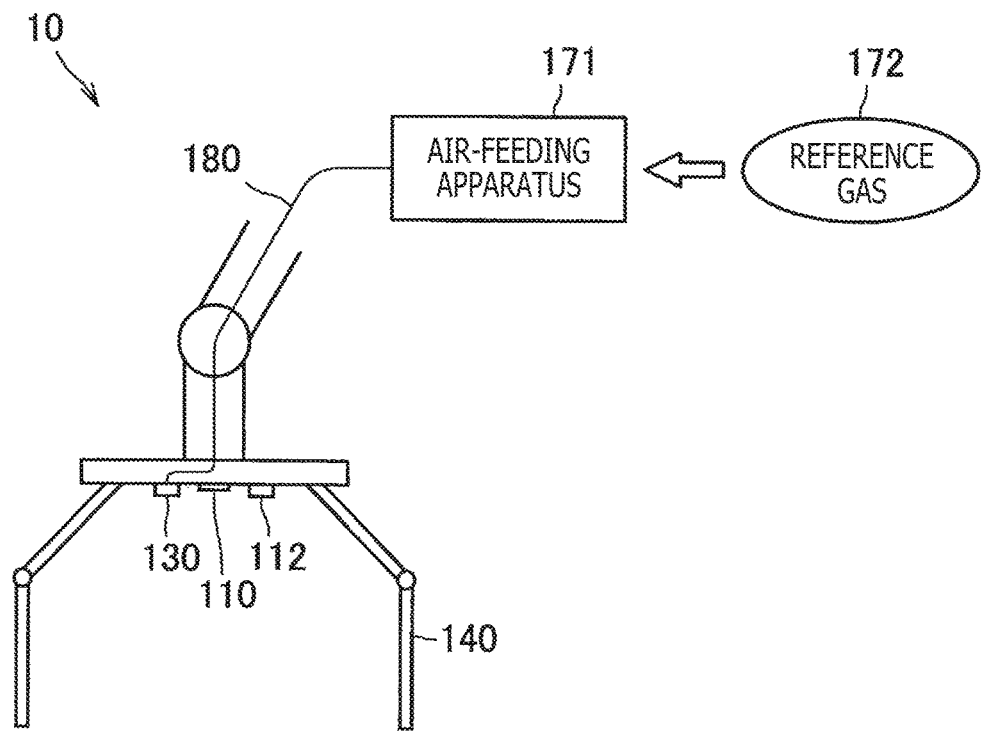
FIG. 1 is a figure depicting a configuration example of an arm apparatus according to an embodiment of the present disclosure.

Hereinafter, suitable embodiments of the present disclosure are explained in detail with reference to the attached figures. Note that, in this specification, and the figures, overlapping explanations are omitted by giving identical reference characters to constituent elements having substantially identical functional configurations.

In addition, in this specification, and the figures, distinctions between a plurality of constituent elements having substantially identical or similar functional configurations are made by giving different numerals after identical reference characters, in some cases. However, it should be noted that only the identical reference characters are given in a case where it is not necessary to make particular distinctions between individual ones of the plurality of constituent elements having the substantially identical or similar functional configurations. In addition, distinctions between similar constituent elements in different embodiments are made by giving different alphabets after identical reference characters, in some cases. However, it should be noted that only the identical reference characters are given in a case where it is not necessary to make particular distinctions between individual ones of the similar constituent elements.

Note that explanations are given in the following order.

0. Overview
1. Details of Embodiment
    1.1. Configuration Example of Arm Apparatus
    1.2. Functional Configuration Example of System
    1.3. Functional Details of System
    1.4. Operation Example of System
2. Modification Examples
    2.1. Functional Details of System according to First Modification Example
    2.2. Functional Details of System according to Second Modification Example
    2.3. Functional Details of System according to Third Modification Example
    2.4. Functional Details of System according to Fourth Modification Example
    2.5. Functional Details of System according to Fifth Modification Example
3. Conclusion

0. OVERVIEW

First, the overview of an embodiment of the present disclosure is explained. In recent years, there are known technologies for managing target objects. For example, as an example of technologies for managing target objects, there are known technologies for managing target objects on the basis of the freshness of the target objects. There are several known technologies for managing target objects on the basis of the freshness of target objects.

As the first technology, there is a known technology in which the freshness of target objects is determined by using image recognition, and the target objects are managed on the basis of the determined freshness. For example, there is a disclosed technology in which the shapes of target objects are recognized by image recognition, and the target objects are sorted out on the basis of the recognized shapes (see PTL 2 described above, for example). Here, in order to highly precisely determine the freshness of the target objects by using image recognition, it is necessary to analyze the external appearance of the target objects by capturing images of the target objects from every direction. However, it is difficult to analyze the ground-contacting surfaces of the target objects by capturing images of the ground-contacting surfaces. In view of this, in order to analyze the ground-contacting surfaces of the target objects by capturing images of the ground-contacting surfaces, it is necessary to make the ground-contacting surfaces exposed by applying some physical action to the target objects (e.g., physical action such as lifting the target objects or rolling the target objects).

However, if physical action is applied to the target objects, there are possibilities that the target objects are damaged, deterioration of the freshness (and external appearance) of the target objects is caused, and so on. Accordingly, physical action is applied to the target objects only to a minimum necessary extent, desirably. Furthermore, in a case where a plurality of target objects are displayed densely, there will be more areas where it is difficult to capture images of the external appearance of the target objects, and so freshness determination of the target objects by using image recognition becomes difficult.

As the second technology, there is a known technology in which IC tags on which the freshness of target objects is recorded are attached to the target objects, and the target objects are managed on the basis of the freshness recorded on the IC tags. For example, there is a disclosed technology in which IC tag information of target objects is read out from IC tags attached to the target objects, and the target objects are moved to predetermined locations on the basis of the IC tag information having been read out (see PTL 1 described above, for example). However, the IC tags become offline after the IC tags are attached to the target objects, and so the freshness recorded on the IC tags is not updated. Accordingly, even if the freshness of the target objects has changed due to the influence of environment temperature or objects (e.g., foods, etc.) near the target objects after the IC tags are attached to the target objects, the IC tags do not reflect the changed freshness.

For example, it is supposed that foods are sold on the basis of the freshness recorded on IC tags at an unmanned store (a store where clerks are absent). In that case, even if the freshness of the foods has changed significantly due to some disturbance after the foods are displayed, the freshness recorded on the IC tags does not reflect the changed freshness, and so it is not possible to sell the foods according to the current freshness of the foods.

As the third technology, there is a known technology in which the freshness of fishes is determined by using a bioelectrical impedance method. Here, the bioelectrical impedance method is a technique in which the freshness of living forms is determined from results of measurement of the resistance values of the living forms. However, defrosted products have changed resistance values of living forms due to destruction of cell membranes accompanying freezing. Accordingly, it is not possible to accurately determine the freshness of defrosted products in a case where the bioelectrical impedance method is used.

In view of this, a technology for more highly precisely executing operation suited for target objects is mainly explained in an embodiment of the present disclosure. More specifically, a technology for more highly precisely executing operation suited for target objects by more highly precisely determining the freshness of the target objects is explained in the embodiment of the present disclosure. In addition, a technology for reducing labor costs by executing operation suited for target objects automatically is explained in the embodiment of the present disclosure.

Note that it is mainly supposed in the embodiment of the present disclosure that the target objects are foods. Furthermore, it is mainly supposed in the embodiment of the present disclosure that the target objects are perishable foods (particularly, fruits) as an example of foods. However, the type of foods is not limited in a case where the target objects are foods. For example, the type of foods may be perishable foods (e.g., vegetables, seafoods, etc.), or may be other foods. In addition, the target objects are not limited to foods. For example, the target objects may be non-food objects (e.g., products, components, etc.).

In addition, in the embodiment of the present disclosure, it is supposed that the target objects are sold at an unmanned store (a store where clerks are absent), and it is mainly supposed that the target objects are placed on shelves (e.g., food display shelves) of the unmanned store. However, the location where the target objects are present is not limited to an unmanned store. For example, supposing that the target objects are sold at a manned store (a store where clerks are present), the target objects may be placed on shelves of the manned store. Alternatively, in a case where the target objects are non-food objects (e.g., products, components, etc.), the target objects may be present at a factory or the like. Alternatively, supposing that the target objects are sold on an online shop, the target objects may be placed on stock shelves (warehouse) of the online shop.

The overview of the embodiment of the present disclosure has been explained thus far.

1. DETAILS OF EMBODIMENT

[1.1. Configuration Example of Arm Apparatus]

A system according to an embodiment of the present disclosure has an arm apparatus (also called a "robot arm apparatus"), and a control apparatus. The arm apparatus senses odor data of a target object by using an odor sensor. In addition, on the basis of the odor data of the target object sensed by the odor sensor, the control apparatus determines the freshness of the target object. Then, on the basis of the determined freshness of the target object, the control apparatus performs control such that operation predefined for the target object is executed. The control apparatus performs operation of controlling the arm apparatus, as an example of the predefined operation. According to the configuration, operation suited for the target object can be executed more highly precisely.

More specifically, because the freshness of the target object is determined on the basis of the odor data of the target object according to the configuration, the freshness of the target object can be determined highly precisely even without applying physical action to the target object, as compared with a case that the freshness is determined by using image recognition. In addition, because the freshness of the target object is determined on the basis of the odor data of the target object according to the configuration, the freshness of the target object is determined highly precisely as compared with a case that freshness recorded on an IC tag is read out, and a case that a bioelectrical impedance method is used. In addition, according to the configuration, it becomes possible to reduce labor costs by executing operation suited for the target object automatically.

Next, a configuration example of the arm apparatus according to the embodiment of the present disclosure is explained with reference to the figures. FIG. 1 is a FIG. depicting the configuration example of the arm apparatus according to the embodiment of the present disclosure. As depicted in FIG. 1, an arm apparatus 10 has an odor sensor 110, an image sensor 112, a nozzle 130, a gripper 140, an air-feeding apparatus 171, and an air-feeding tube 180.

The odor sensor 110 senses the odor data of the target object. Specifically, the odor sensor 110 has a sensor, and senses the odor data of the target object by using the sensor. The odor data sensed by the odor sensor 110 can be used for freshness determination of the target object. Here, the type of the sensor provided to the odor sensor 110 is not limited. For example, it is sufficient if the odor sensor 110 has a sensor that senses rotten odors. By using the sensor that senses rotten odors, the freshness of every target object can be sensed. Alternatively, the odor sensor 110 may have different sensors for different types of target object.

It is mainly supposed in the embodiment of the present disclosure that, as depicted in FIG. 1, the odor sensor 110 is provided on the inner side of the gripper 140. If the odor sensor 110 is provided on the inner side of the gripper 140, the odor sensor 110 can more highly precisely sense the odor data of the target object gripped by the gripper 140. However, the position where the odor sensor 110 is provided is not limited. For example, the odor sensor 110 may be provided on the outer side of the gripper 140 on the arm apparatus 10. Alternatively, as explained later also, the odor sensor 110 may be provided at a position (e.g., a shelf, etc.) not on the arm apparatus 10.

The image sensor 112 has an image sensor and obtains an image by performing image-capturing by using the image sensor. The type of the image sensor is not limited. For example, the image sensor may include a sensor that senses visible light and may include a sensor that senses infrared light. In the embodiment of the present disclosure, it is supposed that the image obtained by the image sensor 112 is used for determination of the type of the target object but is not used for freshness determination of the target object. However, the image obtained by the image sensor 112 may be used also for freshness determination of the target object along with the odor data sensed by the odor sensor 110.

It is mainly supposed in the embodiment of the present disclosure that, as depicted in FIG. 1, the image sensor 112 is provided on the inner side of the gripper 140. If the image sensor 112 is provided on the inner side of the gripper 140, the image sensor 112 can acquire an image of the target object that the gripper 140 faces. However, the position where the image sensor 112 is provided is not limited. For example, the image sensor 112 may be provided on the outer side of the gripper 140 on the arm apparatus 10. Alternatively, the image sensor 112 may be provided at a position (e.g., a ceiling, etc.) not on the arm apparatus 10.

The air-feeding apparatus 171 feeds a reference gas 172 to the air-feeding tube 180. For example, the air-feeding apparatus 171 may have a fan and feed the reference gas 172 to the air-feeding tube 180 by using rotation of the fan. However, the specific configuration of the air-feeding apparatus 171 is not limited.

The reference gas 172 is a gas serving as a reference for the odor measurement of the target object (odor data sensing of the target object). Here, components of a gas included in the reference gas 172 are not limited. The reference gas 172 may be a gas whose odor components are known or may be any gas not containing odor components that influence the freshness determination of the target object. For example, the reference gas 172 may be sealed in in a gas cylinder and fed to the air-feeding apparatus 171 from the gas cylinder.

The air-feeding tube 180 carries the reference gas 172 fed in from the air-feeding apparatus 171 to the nozzle 130.

The nozzle 130 releases the reference gas 172 carried through the air-feeding tube 180 to the outside. The reference gas 172 released from the nozzle 130 is used for blowing away air that is present around the target object. If the odor of the target object is measured after the air that is present around the target object is blown away, the odor of the target object can be measured more highly precisely. For example, adjustments of the amount of the reference gas 172 released outside from the nozzle 130 can be realized by adjusting the restrictor of the nozzle 130.

It is mainly supposed in the embodiment of the present disclosure that, as depicted in FIG. 1, the nozzle 130 is provided on the inner side of the gripper 140. If the nozzle 130 is provided on the inner side of the gripper 140, the nozzle 130 can spray the reference gas 172 to the target object that the gripper 140 faces. However, the position where the nozzle 130 is provided is not limited. For example, the nozzle 130 may be provided on the outer side of the gripper 140 on the arm apparatus 10. Alternatively, the nozzle 130 may be provided at a position not on the arm apparatus 10. Hereinbelow, spraying of the reference gas 172 is also called "air blow."

The gripper 140 grips the target object. In addition, after moving the target object while gripping the target object, the gripper 140 releases the target object at a predetermined position. Thereby, the target object is moved to the predetermined location. Note that the configuration to grip the target object is not limited to the gripper 140. For example, instead of gripping of the target object by the gripper 140, the target object may be gripped by suction of the target object by one or more air-suction apparatuses.

Here, the movement of the gripper 140 can be realized by control of joint sections of the arm apparatus 10. In addition, while it is mainly supposed in the embodiment of the present disclosure that the arm apparatus 10 is suspended from a ceiling surface, the arm apparatus 10 may be fixed to anywhere. For example, the arm apparatus 10 may be fixed to a wall surface. Alternatively, the arm apparatus 10 may not be fixed (the whole may be movable). For example, wheels may be attached to the arm apparatus 10, and rotation of the wheels may enable movement of the arm apparatus 10 on a floor surface or rails.

The movement of the target object may be realized by a technique other than the movement of the gripper 140. For example, movement of a surface (e.g., a shelf, etc.) on which the target object is placed may move the target object. Hereinafter, a detailed configuration example of the arm apparatus 10 is explained. Specifically, a first configuration example and a second configuration example of the arm apparatus 10 are explained. However, the configuration of the arm apparatus 10 is not limited to the following first configuration example and second configuration example.

Figure 2:
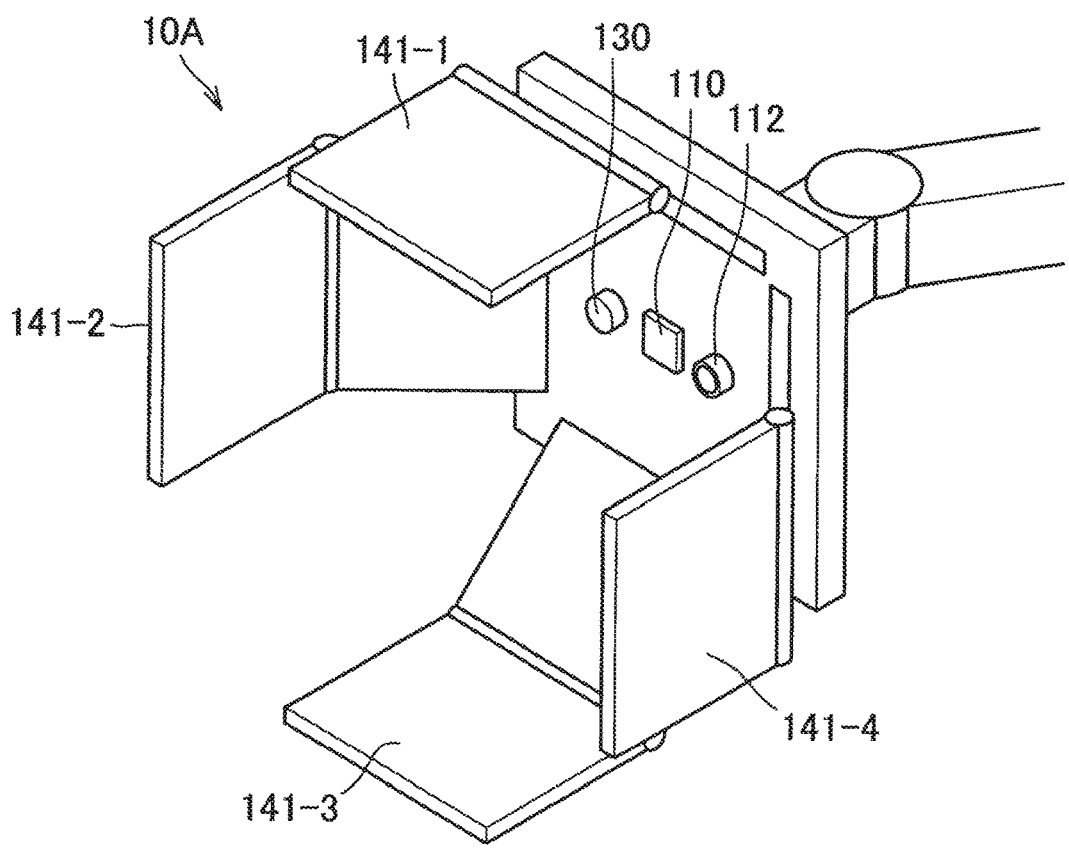
FIG. 2 is an external perspective view depicting a first configuration example of the arm apparatus.
Figure 3:
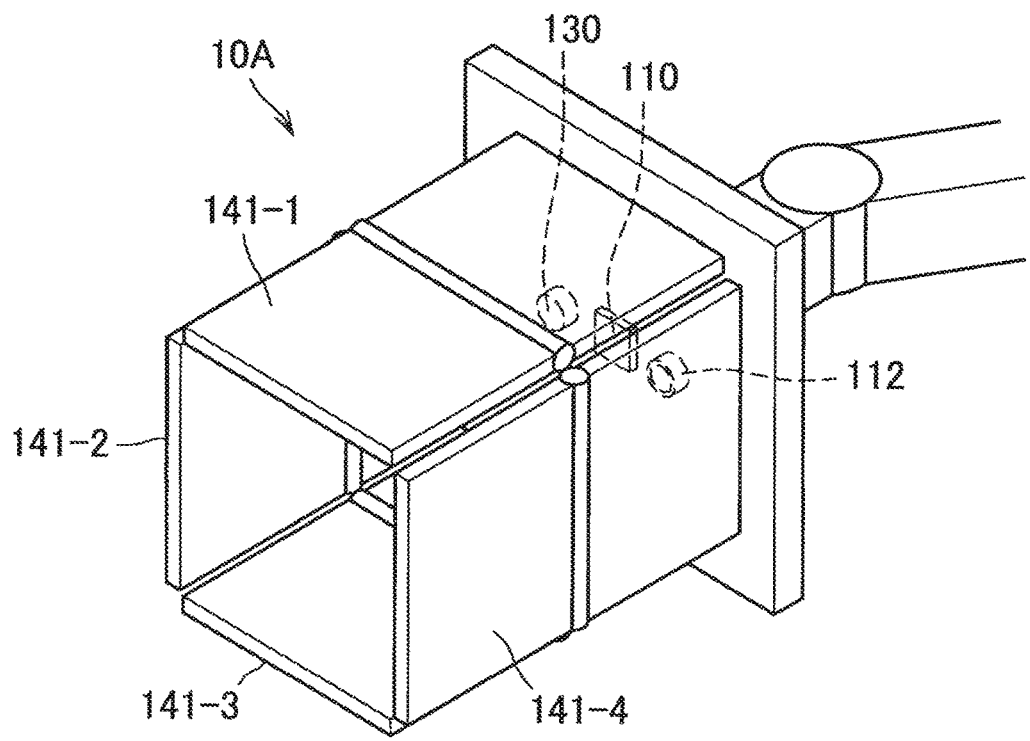
FIG. 3 is an external perspective view depicting the first configuration example of the arm apparatus.

FIG. 2 and FIG. 3 are external perspective views depicting the first configuration example of the arm apparatus 10. As can be seen by referring to FIG. 2 and FIG. 3, an arm apparatus 10A is depicted as the first configuration example of the arm apparatus 10. The arm apparatus 10A in the state depicted in FIG. 2 is not gripping a target object (the state where the gripper 140 is opened). On the other hand, the arm apparatus 10A in the state depicted in FIG. 3 is gripping a target object (the state where the gripper 140 is closed).

As can be seen by referring to FIG. 2 and FIG. 3, the tip of the arm apparatus 10A is provided with fingers 141-1 to 141-4 as the gripper 140. Here, the number of the fingers 141 is not limited to four but it is sufficient if the number of fingers is one or larger. In addition, while each of the fingers 141-1 to 141-4 is provided with two joints (joints at the root of the finger, and the middle of the finger), the number of joints provided to each of the fingers 141-1 to 141-4 is also not limited. As depicted in FIG. 2, there are intervals between the fingers 141-1 to 141-4 in the state where the arm apparatus 10A is not gripping a target object (the state where the gripper 140 is opened).

On the other hand, as depicted in FIG. 3, there are no intervals between the fingers 141-1 to 141-4 in the state where the arm apparatus 10A is gripping a target object (the state where the gripper 140 is closed). If there are no intervals between the fingers 141-1 to 141-4, the fingers 141-1 to 141-4 can block an air inflow from the outer side to the inner side of the gripper 140. In this manner, the shape of the gripper 140 may change into a shape that can block an air inflow from the outer side to the inner side of the gripper 140 when the gripper 140 grips a target object. Thereby, the odor sensor 110 that is present on the inner side of the gripper 140 can more highly precisely sense odor data of the target object.

Figure 4:
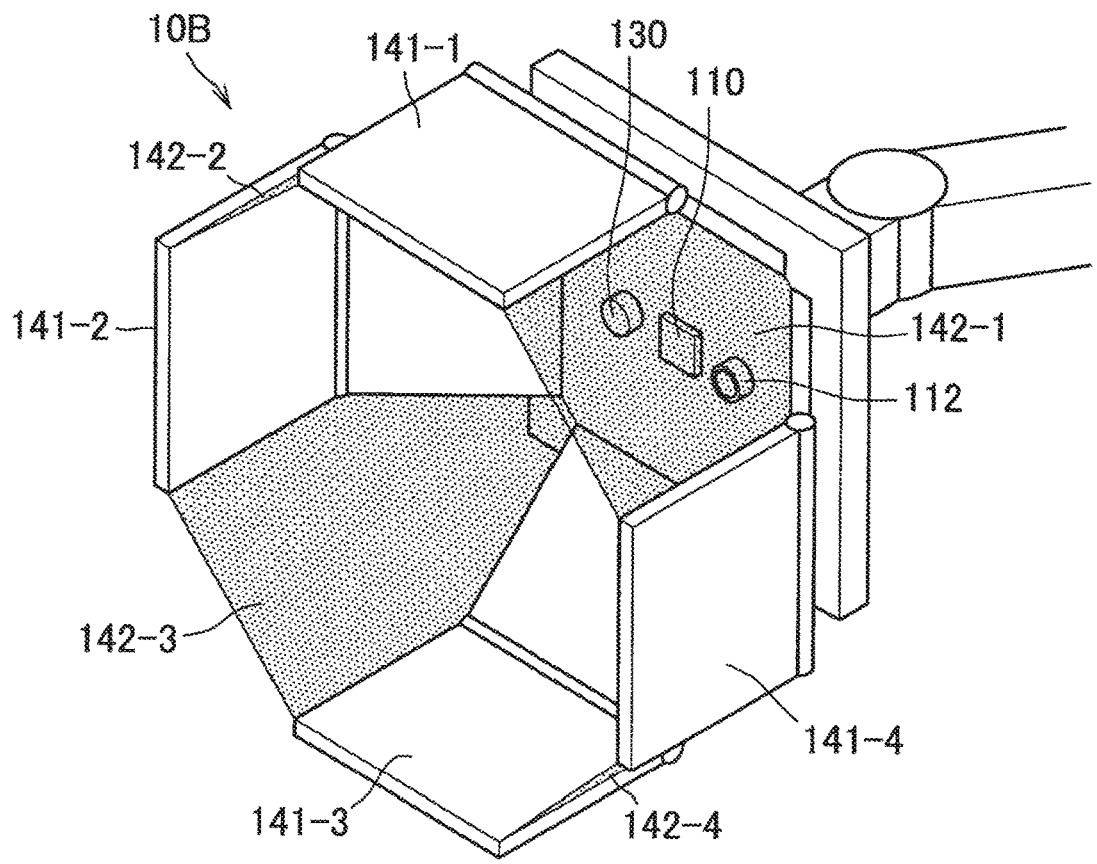
FIG. 4 is an external perspective view depicting a second configuration example of the arm apparatus.

FIG. 4 is an external perspective view depicting a second configuration example of the arm apparatus 10. As can be seen by referring to FIG. 4, an arm apparatus 10B is depicted as the second configuration example of the arm apparatus 10. The arm apparatus 10B in the state depicted in FIG. 4 is not gripping a target object (the state where the gripper 140 is opened). As can be seen by referring to FIG. 4, the tip of the arm apparatus 10B is provided with the fingers 141-1 to 141-4 as the gripper 140. The number of fingers 141 and the number of joints provided to each finger 141 are not limited.

As depicted in FIG. 4, there are intervals between the fingers 141-1 to 141-4 in the state where the arm apparatus 10B is not gripping a target object (the state where the gripper 140 is opened). However, blocking members 142-1 to 142-4 are provided between the fingers 141-1 to 141-4. Thereby, in the state where the arm apparatus 10B is gripping a target object (the state where the gripper 140 is closed), the blocking members 142-1 to 142-4 can block an air inflow from the outer side to the inner side of the gripper 140. Thereby, the odor sensor 110 that is present on the inner side of the gripper 140 can more highly precisely sense odor data of the target object.

Configuration examples of the arm apparatus 10 according to the embodiment of the present disclosure have been explained thus far.

[1.2. Functional Configuration Example of System]

Figure 5:
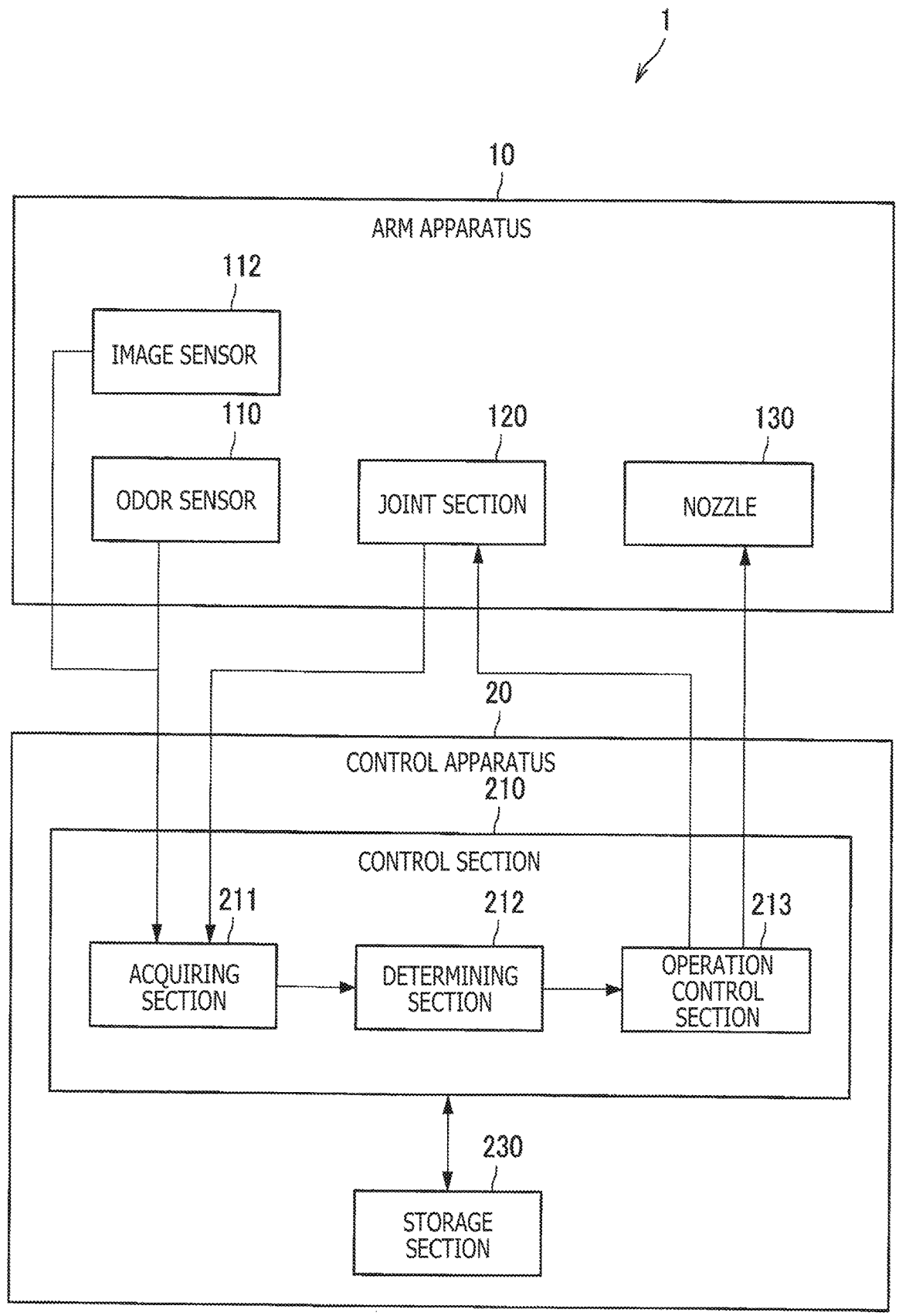
FIG. 5 is a figure depicting a functional configuration example of a system according to the embodiment of the present disclosure.

Next, a functional configuration example of a system 1 according to the embodiment of the present disclosure is explained. FIG. 5 is a figure depicting the functional configuration example of the system 1 according to the embodiment of the present disclosure. As depicted in FIG. 5, the system 1 has the arm apparatus 10, and a control apparatus 20. The arm apparatus 10 has the odor sensor 110, the image sensor 112, a joint section 120, and the nozzle 130. The joint section 120 can be driven by an actuator such as a motor. The joint section 120 includes joints of each of the gripper 140, and the arm. The number of joints, the degree of freedom and movable range of each joint, and the like are not limited.

The control apparatus 20 has a control section 210 and a storage section 230. The control section 210 has an acquiring section 211, a determining section 212, and an operation control section 213.

The control section 210 executes control of each section of the control apparatus 20. The control section 210 may include one or more CPUs (Central Processing Units), and the like, for example. In a case where the control section 210 includes a processing unit such as a CPU, the processing unit may include an electronic circuit. The control section 210 can be realized by a program being executed by the processing unit.

The storage section 230 is a recording medium that includes a memory, and stores a program to be executed by the control section 210, stores data necessary for the execution of the program, and so on. In addition, the storage section 230 temporarily stores data for calculations by the control section 210. The storage section 230 includes a magnetic storage section device, a semiconductor storage device, an optical storage device, a magneto-optical storage device, or the like.

The acquiring section 211 acquires odor data of a target object sensed by the odor sensor 110. The odor data of the target object sensed by the odor sensor 110 is output to the determining section 212. In addition, the acquiring section 211 acquires image data obtained by the image sensor 112. The image data obtained by the image sensor 112 is output to the determining section 212. In addition, the acquiring section 211 acquires the state of the joint section 120 (the position and angle of each joint, etc.). The state of the joint section 120 is output to the determining section 212.

The determining section 212 determines the freshness of the target object on the basis of the odor data of the target object input from the acquiring section 211. In addition, the determining section 212 determines the type of the target object on the basis of the image data input from the acquiring section 211. Models for determining the types of target objects may be constructed in advance through machine learning on the basis of image data for training and teacher data in which target objects are captured. In addition, the determining section 212 can also determine the position of the target object on the basis of the image data. It becomes possible for the gripper 140 to more surely grip the target object by determining the position of the target object from the image data. However, the position of the target object may be grasped in advance.

The operation control section 213 performs control such that operation predefined for the target object is executed on the basis of the freshness of the target object determined by the determining section 212. It is mainly supposed in the embodiment of the present disclosure that the operation control section 213 performs control such that the target object is moved on the basis of the freshness of the target object. Specifically, with reference to the state of the joint section 120, the operation control section 213 performs control such that the actuator of the arm apparatus 10 drives the joint section 120. Thereby, the target object is gripped and moved by the gripper 140.

In addition, the operation control section 213 performs control such that the reference gas is sprayed onto the target object before odor data is sensed by the odor sensor 110. At this time, it is supposed that a suited amount of the reference gas differs according to the type of the target object. For example, the amount of the reference gas to be sprayed onto a food whose surface is dredged with a material that can fly away easily due to a wind pressure (e.g., sugar, dried bonito shavings, etc.) is desirably relatively small. On the other hand, the amount of the reference gas to be sprayed onto a food whose surface is free of a material that can fly away easily due to a wind pressure (e.g., a food in a box, etc.) is desirably relatively large. In view of this, the operation control section 213 desirably adjusts the amount of the reference gas according to the type of the target object.

A functional configuration example of the system 1 according to the embodiment of the present disclosure has been explained thus far.

[1.3. Functional Details of System]

Figure 6:
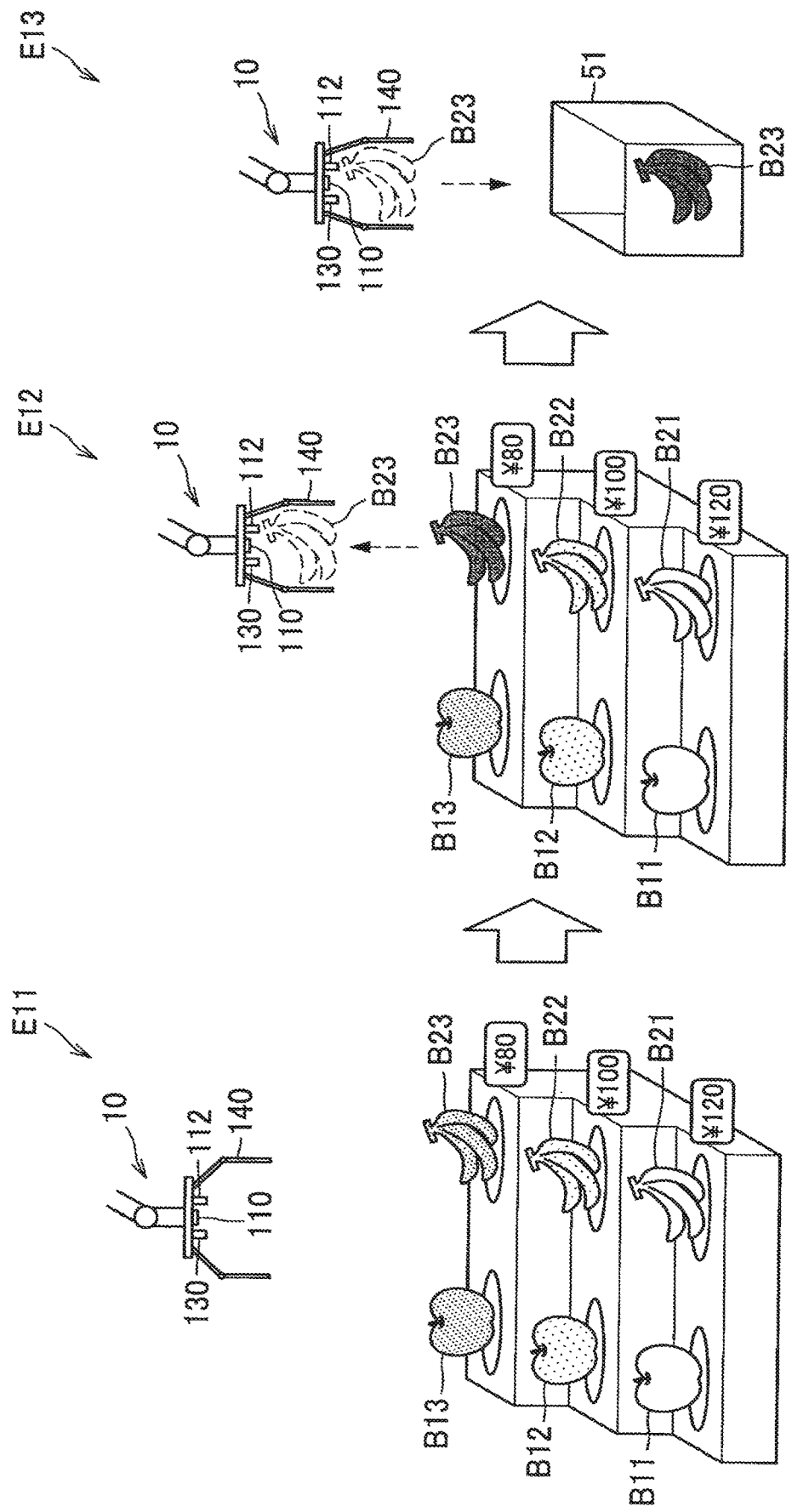
FIG. 6 is a figure for explaining functional details of the system according to the embodiment of the present disclosure.

Next, functional details of the system 1 according to the embodiment of the present disclosure are explained. FIG. 6 is a figure for explaining the functional details of the system 1 according to the embodiment of the present disclosure. As can be seen by referring to FIG. 6, target objects B11 to B13 and target objects B21 to B23 are placed on shelves of a store E11. In addition, the arm apparatus 10 suspended from a ceiling surface is present in the store E11. The target objects B11 to B13 are apples, and the target objects B21 to B23 are bananas. However, as described above, the target objects B11 to B13 and the target objects B21 to B23 are not limited to fruits.

The target object B11 and the target object B21 have the highest freshness. Accordingly, the target object B11 and the target object B21 are associated with the highest price (120 yen in the example depicted in FIG. 6). The target object B12 and the target object B22 have the next highest freshness. Accordingly, the target object B12 and the target object B22 are associated with the next highest price (100 yen in the example depicted in FIG. 6). The target object B13 and the target object B23 have the lowest freshness. Accordingly, the target object B13 and the target object B23 are associated with the lowest price (80 yen in the example depicted in FIG. 6). Price tags on which the individual prices (120 yen, 100 yen, and 80 yen) are written are placed on the shelves.

As can be seen by referring to FIG. 6, a store E12 in a state after a lapse of time after the state of the store E11 is depicted. Similarly, the target objects B11 to B13 and the target objects B21 to B23 are placed on the shelves of the store E12. However, the freshness of the target object B23 has lowered further, and the freshness of the target object B23 has become lower than a first threshold. The target object B23 having freshness that has become lower than the first threshold should be treated a disposed article.

The operation control section 213 controls the arm apparatus 10 such that the arm apparatus 10 reaches for the target object B23 at a predetermined timing. The predetermined timing is not limited. For example, the predetermined timing may be after a lapse of a predetermined length of time. Alternatively, the predetermined timing may be a timing at which a customer has decided to purchase the target object B23 as an item, and the target object B23 is carried to a checkout counter.

Then, the acquiring section 211 acquires image data (first image data) obtained by the image sensor 112. The determining section 212 determines the type of the target object B23 on the basis of the image data. It is mainly supposed here that the amount of the reference gas to be sprayed onto the target object B23 is adjusted according to the type of the target object B23. However, another parameter may change according to the type of the target object B23. For example, the first threshold to be compared with the freshness may change according to the type of the target object B23. Alternatively, a correspondence between odor data and the freshness may change according to the type of the target object B23.

The operation control section 213 controls the nozzle 130 such that the reference gas is sprayed onto the target object B23. By blowing away air that is present around the target object B23, and then measuring the odor of the target object B23, the odor of the target object B23 can be measured more highly precisely (e.g., the possibility of treating the target object B23 as a disposed article by mistake although the target object B23 is not a disposed article is lowered). Then, the odor sensor 110 senses odor data of the target object B23. The acquiring section 211 acquires the odor data (first odor data) of the target object sensed by the odor sensor 110.

In addition, the determining section 212 determines the freshness (first freshness) of the target object B23 on the basis of the odor data. Then, the determining section 212 determines whether or not the freshness satisfies a predetermined condition. Here, the predetermined condition is not limited. It is mainly supposed in the example depicted in FIG. 6 that the target object B23 having freshness that has become lower than the first threshold is treated as a disposed article, and accordingly the determining section 212 determines whether or not the freshness is lower than the first threshold. However, the determining section 212 may determine whether or not the freshness is higher than the first threshold.

In a case where the freshness does not satisfy the predetermined condition, the operation control section 213 controls the arm apparatus 10 such that the arm apparatus 10 reaches for the next target object without performing anything on the target object B23. Then, a similar process is executed also on the next target object. On the other hand, in a case where the freshness satisfies the predetermined condition, the operation control section 213 controls the arm apparatus 10 such that the target object B23 is gripped and lifted by the gripper 140. More specifically, in a case where the freshness is lower than the first threshold, the operation control section 213 controls the arm apparatus 10 such that the target object B23 is gripped and lifted by the gripper 140.

If odor measurement is performed on the target object B23 lifted in this manner, the odor measurement of the target object B23 is performed at a position away from other target objects that are present near the target object B23, and so the odor of the target object B23 is measured more highly precisely (e.g., the possibility of treating the target object B23 as a disposed article by mistake although the target object B23 is not a disposed article is lowered). Then, by lifting only the target object B23 determined as having freshness that is lower than the first threshold as in this example, physical action to be applied to the target object B23 can be reduced. However, in a case where the robustness of the target object B23 against physical action is high, or in other similar cases, the target object B23 may be lifted from the beginning to measure the odor of the target object B23.

The operation control section 213 controls the nozzle 130 such that the reference gas is sprayed onto the target object B23 again. Then, the odor sensor 110 senses odor data (second odor data) of the target object B23 while the target object B23 is being gripped and lifted by the gripper 140. Then, the determining section 212 determines the freshness (second freshness) of the target object B23 on the basis of the odor data. Similarly, the determining section 212 determines whether or not the freshness satisfies a predetermined condition. It is mainly supposed here also that the determining section 212 determines whether or not the freshness is lower than the first threshold. However, the determining section 212 may determine whether or not the freshness is higher than the first threshold.

In a case where the freshness does not satisfy the predetermined condition, the operation control section 213 controls the arm apparatus 10 such that the arm apparatus 10 reaches for the next target object without performing anything on the target object B23. Then, a similar process is executed also on the next target object. On the other hand, in a case where the freshness satisfies the predetermined condition, the operation control section 213 performs control such that the predefined operation is executed. More specifically, in a case where the freshness is lower than the first threshold, the operation control section 213 controls the arm apparatus 10 such that the target object B23 is moved to a predetermined space while the target object B23 is being gripped.

As can be seen by referring to FIG. 6, a store E13 in a state after a lapse of time after the state of the store E12 is depicted. Here, because the freshness is lower than the first threshold, the operation control section 213 controls the arm apparatus 10 such that the arm apparatus 10 moves the target object B23 to a space where disposed articles are placed (a disposed-article space 51) while gripping the target object B23. Then, after the target object B23 is moved to the disposed-article space 51, the operation control section 213 makes the gripping of the target object B23 by the gripper 140 released. Thereby, the target object B23 is placed in the disposed-article space 51. Note that the operation control section 213 may control the arm apparatus 10 such that the arm apparatus 10 moves the target object B23 to a predetermined space in a case where the freshness is higher than the first threshold.

According to the configuration, the freshness of the target object B23 is determined more highly precisely on the basis of the odor data of the target object B23. Thereby, operation suited for the target object B23 can be executed more highly precisely. In addition, according to the configuration, labor costs can be lowered by executing operation suited for the target object B23 automatically. Note that FIG. 6 depicts an example of a process to be executed on the target object B23. However, processes similar to the process on the target object B23 may be executed sequentially also on other target objects (the target objects B11 to B13, B21, and B22).

Details of the functionalities of the system 1 according to the embodiment of the present disclosure have been explained thus far.

[1.4. Operation Example of System]

Figure 7:
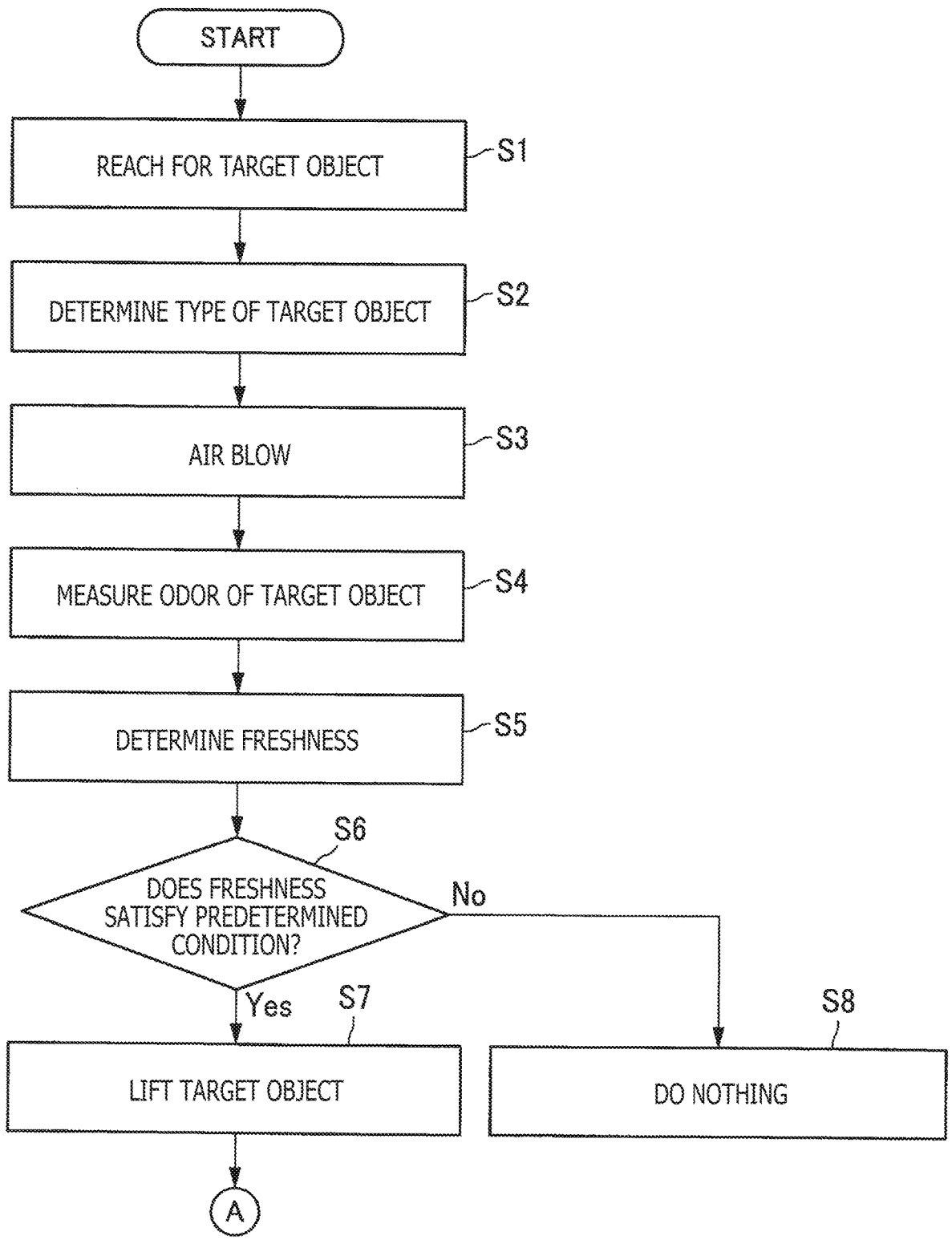
FIG. 7 is a flowchart depicting an operation example of the system according to the embodiment of the present disclosure.
Figure 8:
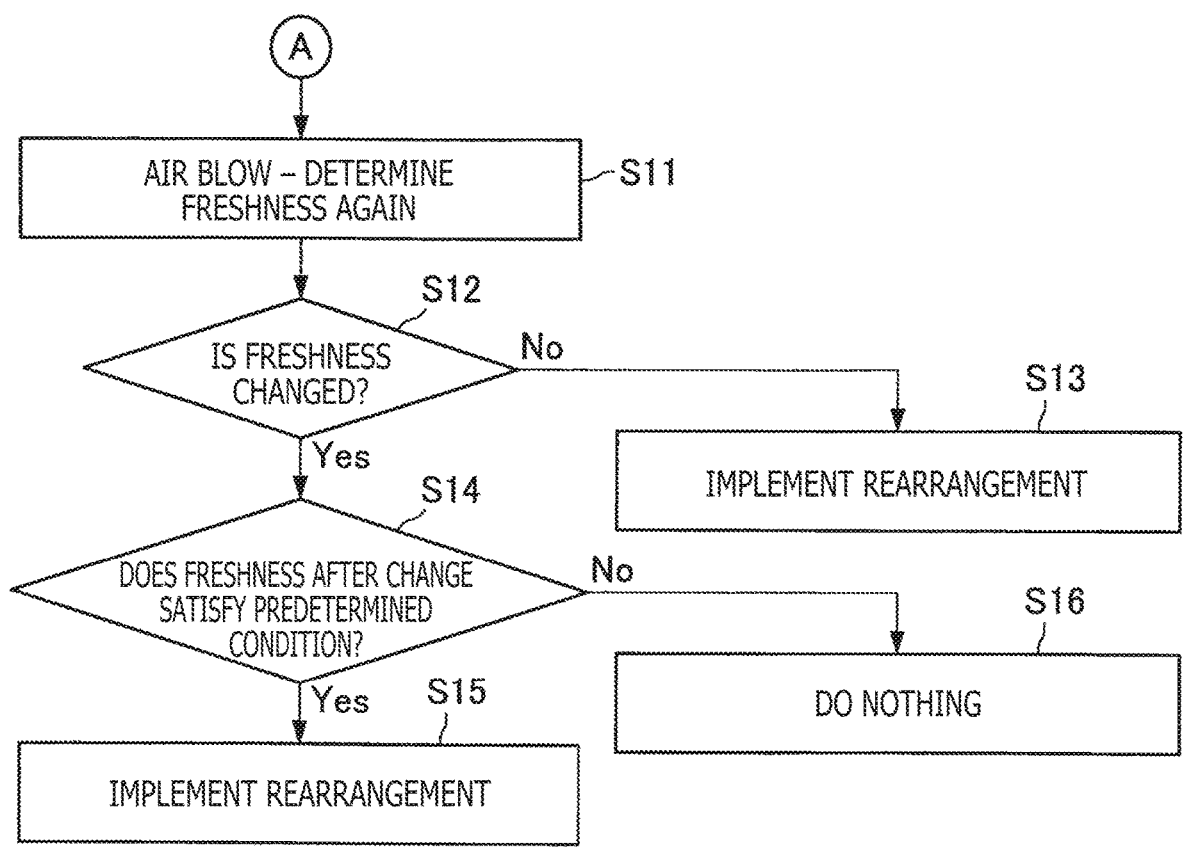
FIG. 8 is a flowchart depicting an operation example of the system according to the embodiment of the present disclosure.

Next, an operation example of the system 1 according to the embodiment of the present disclosure is explained. FIG. 7 and FIG. 8 are flowcharts depicting the operation example of the system 1 according to the embodiment of the present disclosure. Note that the flowcharts depicted in FIG. 7 and FIG. 8 merely depict one example of operation of the system 1 according to the embodiment of the present disclosure. Accordingly, the operation of the system 1 according to the embodiment of the present disclosure is not limited to the example depicted in the flowcharts in FIG. 7 and FIG. 8.

As depicted in FIG. 7, the operation control section 213 controls the arm apparatus 10 such that the arm apparatus 10 reaches for a target object at a predetermined timing (S1). Then, the acquiring section 211 acquires image data (first image data) obtained by the image sensor 112. The determining section 212 determines the type of the target object on the basis of the image data (S2). It is mainly supposed here that the amount of the reference gas to be sprayed onto the target object is adjusted according to the type of the target object. However, as described above, the first threshold to be compared with the freshness may change according to the type of the target object. Alternatively, a correspondence between odor data and the freshness may change according to the type of the target object.

The operation control section 213 performs air blowing (S3). That is, the operation control section 213 controls the nozzle 130 such that the reference gas is sprayed onto the target object. Then, the odor sensor 110 senses odor data of the target object (S4). The acquiring section 211 acquires the odor data (first odor data) of the target object sensed by the odor sensor 110.

In addition, the determining section 212 determines the freshness (first freshness) of the target object on the basis of the odor data (S5). Then, the determining section 212 determines whether or not the freshness satisfies a predetermined condition (S6). In a case where the freshness does not satisfy the predetermined condition ("No" at S6), the operation control section 213 controls the arm apparatus 10 such that the arm apparatus 10 reaches for the next target object without performing anything on the target object B23 (S8). Then, a similar process is executed also on the next target object. On the other hand, in a case where the freshness satisfies the predetermined condition ("Yes" at S6), the operation control section 213 controls the arm apparatus 10 such that the target object is gripped and lifted by the gripper 140 (S7).

Next, as depicted in FIG. 8, the operation control section 213 performs air blowing again. That is, the operation control section 213 controls the nozzle 130 such that the reference gas is sprayed onto the target object again (S11). Then, the odor sensor 110 senses odor data (second odor data) of the target object while the target object is being gripped and lifted by the gripper 140.

The determining section 212 determines the freshness (second freshness) of the target object B23 on the basis of the odor data (S11). The determining section 212 determines whether the freshness (second freshness) is different from the freshness (first freshness) (S12). In a case where it is determined that the freshness (second freshness) is different from the freshness (first freshness) ("No" at S12), the operation control section 213 implements rearrangement of the target object (S13). In the example depicted in FIG. 6, the rearrangement of the target object corresponds to moving the target object to the disposed-article space 51. In addition, in modification examples explained below, the rearrangement of the target object corresponds to moving a target object to another position of shelves.

On the other hand, in a case where it is determined that the freshness (second freshness) is different from the freshness (first freshness) ("Yes" at S12), the operation control section 213 determines whether or not the changed freshness (second freshness) satisfies the predetermined condition (S14). In a case where the changed freshness (second freshness) does not satisfy the predetermined condition ("No" at S14), the operation control section 213 controls the arm apparatus 10 such that the arm apparatus 10 reaches for the next target object without performing anything on the target object (S16). Then, a similar process is executed also on the next target object. On the other hand, in a case where the changed freshness (second freshness) satisfies the predetermined condition ("Yes" at S14), the operation control section 213 implements rearrangement of the target object (S15).

Note that FIG. 7 and FIG. 8 depict an example of a process executed on one target object. However, similar processes may be executed sequentially also on other target objects.

An operation example of the system 1 according to the embodiment of the present disclosure has been explained thus far.

2. MODIFICATION EXAMPLES

Next, various types of modification example are explained. Note that a first modification example and a second modification example correspond to examples in which operation according to the freshness of one target object is executed, similarly to the example described above. Specifically, it is supposed that target objects having freshness lower than a second threshold are associated with a second price (80 yen), target objects having freshness higher than the second threshold and lower than a third threshold are associated with a first price (100 yen), and target objects having freshness higher than the third threshold are associated with a third price (120 yen). On the other hand, a third modification example and a fourth modification example correspond to examples in which operation according to a relation between the freshness of a plurality of target objects is executed. A fifth modification example corresponds to a modification example related to an arrangement of odor sensors.

[2.1. Functional Details of System According to First Modification Example]

Figure 9:
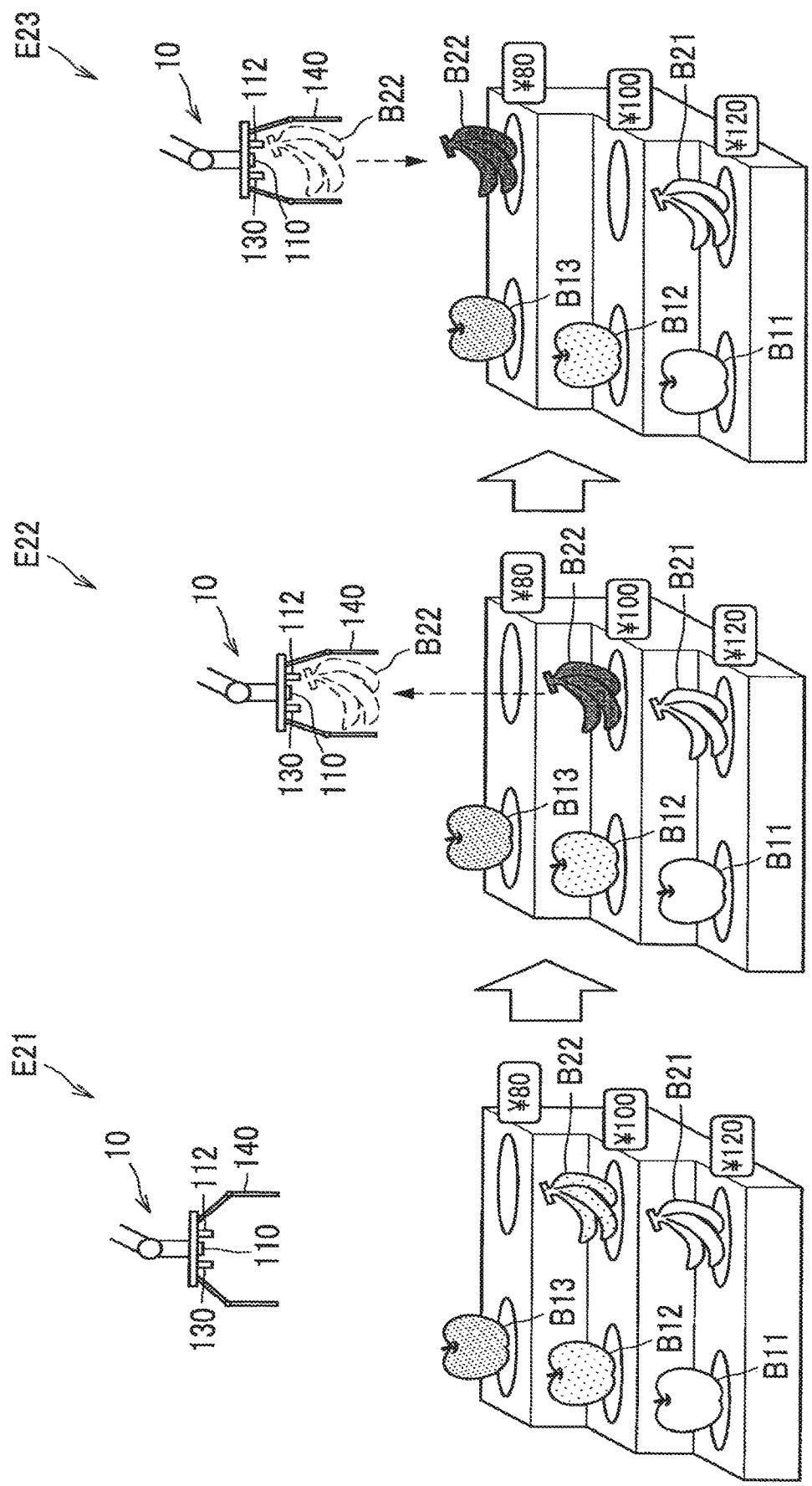
FIG. 9 is a figure for explaining functional details of a system according to a first modification example.

First, functional details of a system according to the first modification example are explained. FIG. 9 is a figure for explaining the functional details of the system according to the first modification example. As can be seen by referring to FIG. 9, the target objects B11 to B13 and target objects B21 to B22 are placed on shelves of a store E21. In addition, the arm apparatus 10 suspended from a ceiling surface is present in the store E21. Similarly to the example explained with reference to FIG. 6, the target objects B11 to B13 and the target objects B21 to B22 are not limited to fruits. In addition, the freshness and price of each of the target objects B11 to B13 and the target objects B21 to B22 are similar to those in the example explained with reference to FIG. 6.

As can be seen by referring to FIG. 9, a store E22 in a state after a lapse of time after the state of the store E21 is depicted. Similarly, the target objects B11 to B13 and the target objects B21 to B22 are placed on the shelves of the store E22. However, the freshness of the target object B22 has lowered further, and the freshness of the target object B22 has become lower than the second threshold. The second threshold is higher than a first threshold for disposal determination. The target object B22 having freshness that has become lower than the second threshold should be placed in a space associated with a predetermined price (e.g., a discounted price). In the example depicted in FIG. 9, the target object B22 should be moved from a space associated with the first price (100 yen) to a space associated with the second price (80 yen).

The operation control section 213 controls the arm apparatus 10 such that the arm apparatus 10 reaches for the target object B22 at a predetermined timing. Similarly to the example explained with reference to FIG. 6, the predetermined timing is not limited.

Then, the acquiring section 211 acquires image data (first image data) obtained by the image sensor 112. The determining section 212 determines the type of the target object B22 on the basis of the image data. It is mainly supposed here that the amount of the reference gas to be sprayed onto the target object B22 is adjusted according to the type of the target object B22. However, similarly to the example explained with reference to FIG. 6, another parameter may change according to the type of the target object B22.

The operation control section 213 controls the nozzle 130 such that the reference gas is sprayed onto the target object B22. Then, the odor sensor 110 senses odor data of the target object B22. The acquiring section 211 acquires the odor data (first odor data) of the target object sensed by the odor sensor 110.

In addition, the determining section 212 determines the freshness (first freshness) of the target object B22 on the basis of the odor data. Then, the determining section 212 determines whether or not the freshness satisfies a predetermined condition. Here, the predetermined condition is not limited. It is mainly supposed in the example depicted in FIG. 9 that in order to move the target object B22 having freshness that has become lower than the second threshold to the space associated with the second price (80 yen), the determining section 212 determines whether or not the freshness is lower than the second threshold. However, the determining section 212 may determine whether or not the freshness is higher than the second threshold.

In a case where the freshness does not satisfy the predetermined condition, the operation control section 213 controls the arm apparatus 10 such that the arm apparatus 10 reaches for the next target object without performing anything on the target object B22. Then, a similar process is executed also on the next target object. On the other hand, in a case where the freshness satisfies the predetermined condition, the operation control section 213 controls the arm apparatus 10 such that the target object B22 is gripped and lifted by the gripper 140. More specifically, in a case where the freshness is lower than the second threshold, the operation control section 213 controls the arm apparatus 10 such that the target object B22 is gripped and lifted by the gripper 140.

However, in a case where the robustness of the target object B22 against physical action is high, or in other similar cases, the target object B22 may be lifted from the beginning to measure the odor of the target object B22.

The operation control section 213 controls the nozzle 130 such that the reference gas is sprayed onto the target object B22 again. Then, the odor sensor 110 senses odor data (second odor data) of the target object B22 while the target object B22 is being gripped and lifted by the gripper 140. Then, the determining section 212 determines the freshness (second freshness) of the target object B22 on the basis of the odor data. Similarly, the determining section 212 determines whether or not the freshness satisfies a predetermined condition. It is mainly supposed here also that the determining section 212 determines whether or not the freshness is lower than the second threshold. However, the determining section 212 may determine whether or not the freshness is higher than the second threshold.

In a case where the freshness does not satisfy the predetermined condition, the operation control section 213 controls the arm apparatus 10 such that the arm apparatus 10 reaches for the next target object without performing anything on the target object B22. Then, a similar process is executed also on the next target object. On the other hand, in a case where the freshness satisfies the predetermined condition, the operation control section 213 performs control such that the predefined operation is executed. More specifically, in a case where the freshness is lower than the second threshold, the operation control section 213 controls the arm apparatus 10 such that the target object B22 is moved to a predetermined space while the target object B22 is being gripped.

As can be seen by referring to FIG. 9, a store E23 in a state after a lapse of time after the state of the store E22 is depicted. Here, because the freshness is lower than the second threshold, the operation control section 213 controls the arm apparatus 10 such that the target object B22 is moved to the space associated with the second price (80 yen) while the target object B22 is being gripped. Then, after the target object B22 is moved to the space associated with the second price (80 yen), the operation control section 213 makes the gripping of the target object B22 by the gripper 140 released. Thereby, the target object B22 is placed in the space associated with the second price (80 yen). Note that the operation control section 213 may control the arm apparatus 10 such that the arm apparatus 10 moves the target object B22 to a predetermined space in a case where the freshness is higher than the second threshold.

Note that FIG. 9 depicts an example of a process to be executed on the target object B22. However, processes similar to the process on the target object B22 may be executed sequentially also on other target objects (the target objects B11 to B13, and B21).

Functional details of the system according to the first modification example have been explained thus far.

[2.2. Functional Details of System According to Second Modification Example]

Figure 10:
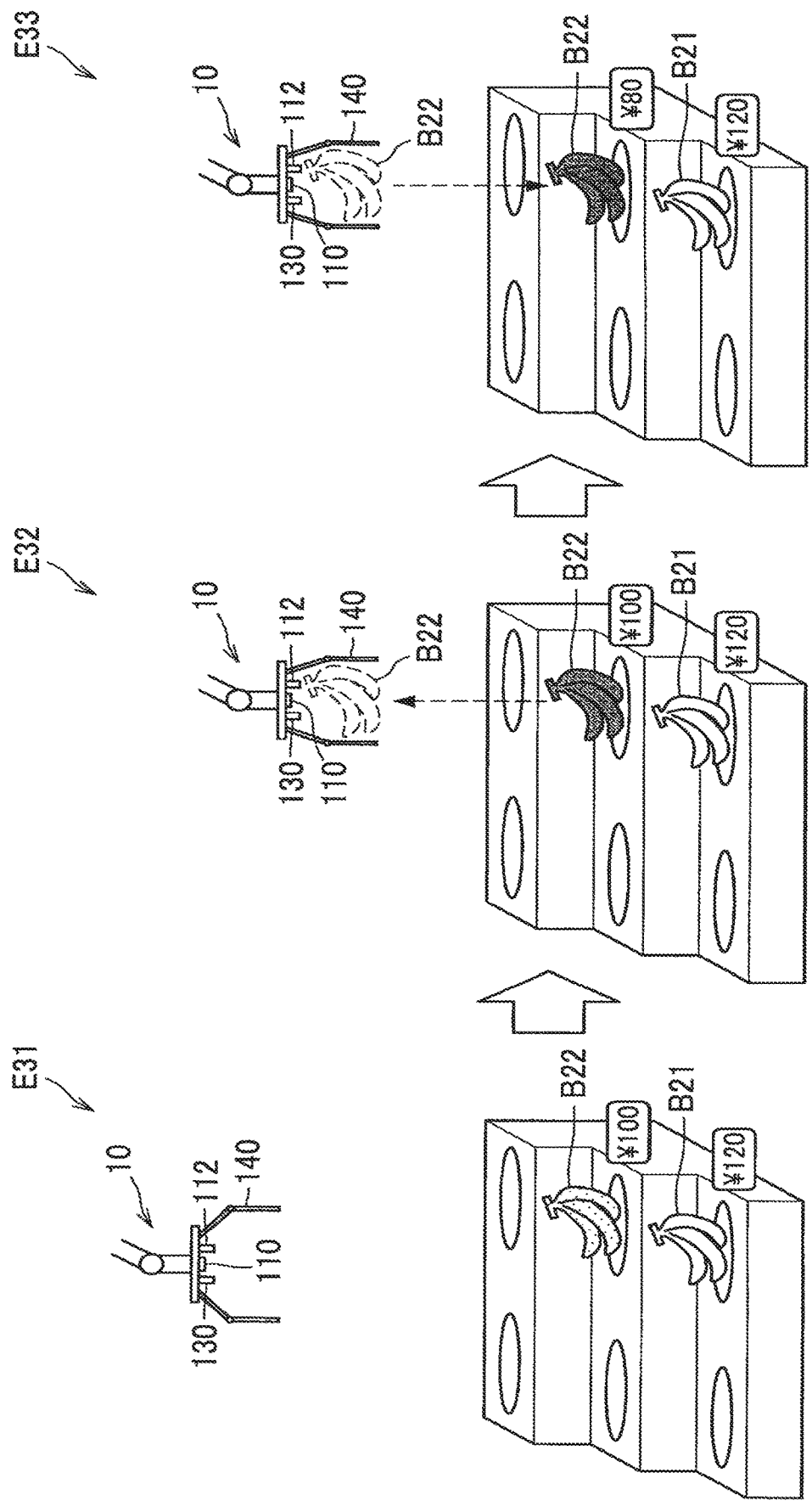
FIG. 10 is a figure for explaining functional details of a system according to a second modification example.

First, functional details of a system according to the second modification example are explained. FIG. 10 is a figure for explaining the functional details of the system according to the second modification example. As can be seen by referring to FIG. 10, the target objects B21 to B22 are placed on shelves of a store E31. In addition, the arm apparatus 10 suspended from a ceiling surface is present in the store E31. Similarly to the example explained with reference to FIG. 6, the target objects B21 to B22 are not limited to fruits. In addition, the freshness and price of each of the target objects B21 to B22 are similar to those in the example explained with reference to FIG. 6.

As can be seen by referring to FIG. 10, a store E32 in a state after a lapse of time after the state of the store E31 is depicted. Similarly, the target objects B21 to B22 are placed on the shelves of the store E32. However, the freshness of the target object B22 has lowered further, and the freshness of the target object B22 has become lower than the second threshold. The target object B22 having freshness that has become lower than the second threshold should be associated with a price according to the freshness. In the example depicted in FIG. 10, the target object B22 should be associated not with the first price (100 yen), but with the second price (80 yen).

The operation control section 213 controls the arm apparatus 10 such that the arm apparatus 10 reaches for the target object B22 at a predetermined timing. Similarly to the example explained with reference to FIG. 6, the predetermined timing is not limited.

Then, the acquiring section 211 acquires image data (first image data) obtained by the image sensor 112. The determining section 212 determines the type of the target object B22 on the basis of the image data. It is mainly supposed here that the amount of the reference gas to be sprayed onto the target object B22 is adjusted according to the type of the target object B22. However, similarly to the example explained with reference to FIG. 6, another parameter may change according to the type of the target object B22.

The operation control section 213 controls the nozzle 130 such that the reference gas is sprayed onto the target object B22. Then, the odor sensor 110 senses odor data of the target object B22. The acquiring section 211 acquires the odor data (first odor data) of the target object sensed by the odor sensor 110.

In addition, the determining section 212 determines the freshness (first freshness) of the target object B22 on the basis of the odor data. Then, the determining section 212 determines whether or not the freshness satisfies a predetermined condition. Here, the predetermined condition is not limited. It is mainly supposed in the example depicted in FIG. 10 that in order to associate the target object B22 having freshness that has become lower than the second threshold with the second price (80 yen), the determining section 212 determines whether or not the freshness is lower than the second threshold. However, the determining section 212 may determine whether or not the freshness is higher than the second threshold.

In a case where the freshness does not satisfy the predetermined condition, the operation control section 213 controls the arm apparatus 10 such that the arm apparatus 10 reaches for the next target object without performing anything on the target object B22. Then, a similar process is executed also on the next target object. On the other hand, in a case where the freshness satisfies the predetermined condition, the operation control section 213 controls the arm apparatus 10 such that the target object B22 is gripped and lifted by the gripper 140. More specifically, in a case where the freshness is lower than the second threshold, the operation control section 213 controls the arm apparatus 10 such that the target object B22 is gripped and lifted by the gripper 140.

However, in a case where the robustness of the target object B22 against physical action is high, or in other similar cases, the target object B22 may be lifted from the beginning to measure the odor of the target object B22.

The operation control section 213 controls the nozzle 130 such that the reference gas is sprayed onto the target object B22 again. Then, the odor sensor 110 senses odor data (second odor data) of the target object B22 while the target object B22 is being gripped and lifted by the gripper 140. Then, the determining section 212 determines the freshness (second freshness) of the target object B22 on the basis of the odor data. Similarly, the determining section 212 determines whether or not the freshness satisfies a predetermined condition. It is mainly supposed here also that the determining section 212 determines whether or not the freshness is lower than the second threshold. However, the determining section 212 may determine whether or not the freshness is higher than the second threshold.

In a case where the freshness does not satisfy the predetermined condition, the operation control section 213 controls the arm apparatus 10 such that the arm apparatus 10 reaches for the next target object without performing anything on the target object B22. Then, a similar process is executed also on the next target object. On the other hand, in a case where the freshness satisfies the predetermined condition, the operation control section 213 performs control such that the predefined operation is executed. More specifically, the operation control section 213 performs control such that the gripping of the target object B22 is released in a case where the freshness is lower than the second threshold, and also performs control such that the target object B22 is associated with the second price (80 yen) according to the freshness.

As can be seen by referring to FIG. 10, a store E33 in a state after a lapse of time after the state of the store E32 is depicted. Here, because the freshness is lower than the second threshold, the operation control section 213 makes the gripping of the target object B22 released, and also performs control such that the target object B22 is associated with the second price (80 yen) according to the freshness. Thereby, the target object B22 is returned to the original space, and the target object B22 is associated with the second price (80 yen). Note that the operation control section 213 may perform control such that a price according to the freshness is associated with the target object B22 in a case where the freshness is higher than the second threshold.

Note that the association of the second price (80 yen) with the target object B22 may be realized in any manner. For example, the operation control section 213 may control the arm apparatus 10 such that a price tag on which the first price (100 yen) is written is moved away from the space in which the target object B22 is placed, and also a price tag on which the second price (80 yen) is written is moved closer to the space in which the target object B22 is placed. Alternatively, the operation control section 213 may control the arm apparatus 10 such that the written price of the price tag associated with the target object B22 is changed from the first price (100 yen) to the second price (80 yen).

In addition, FIG. 10 depicts an example of a process to be executed on the target object B22. However, a process similar to the process on the target object B22 may be executed also on the other target object (the target object B21).

In the example explained with reference to FIG. 10, the operation control section 213 performs control such that a price according to the freshness of a target object is associated with the target object. However, the operation control section 213 may perform control such that another parameter according to the freshness of the target object is associated with the target object. For example, the operation control section 213 may perform control such that a use priority according to the freshness of the target object is associated with the target object. Here, the higher the use priority of the target object is, the more prioritized the target object is when target objects are to be used.

The relation between the freshness and the use priority is not limited. For example, in a case where it is considered that the lower the freshness of the target object is, the more prioritized the target object should be when target objects are to be used, the operation control section 213 may perform control such that a higher use priority is associated with the target object. Alternatively, in a case where it is considered that the higher the freshness of the target object is, the more prioritized the target object should be when target objects are to be used, the operation control section 213 may perform control such that a higher use priority is associated with the target object.

For example, target objects may be used as items to be sold to customers. At this time, in a case where target objects are sold to customers at a store, the operation control section 213 may control the arm apparatus 10 such that the higher the use priority of a target object is, the closer to an aisle where customers pass through the target object is moved. Thereby, it becomes possible to attract attention of customers to the freshness of target objects. Alternatively, in a case where target objects are sold to customers on an online shop (or a store, etc.), the higher the use priority of a target object is, the higher the position of the target object in the sequence of sales to customers may be (the target object may be associated with a higher position in the sequence of sales).

Functional details of the system according to the second modification example have been explained thus far.

[2.3. Functional Details of System According to Third Modification Example]

Figure 11:
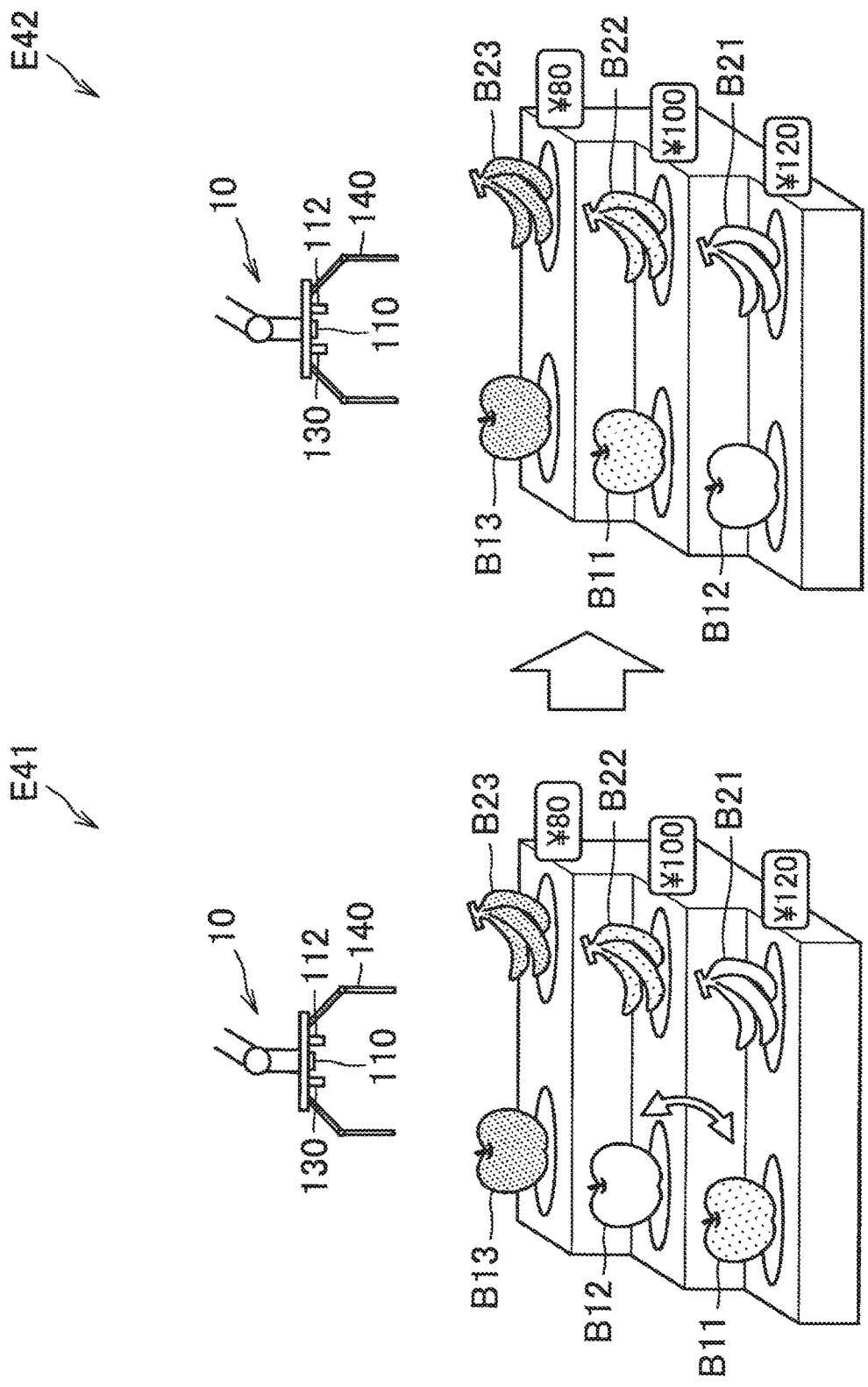
FIG. 11 is a figure for explaining functional details of a system according to a third modification example.

First, functional details of a system according to the third modification example are explained. FIG. 11 is a figure for explaining the functional details of the system according to the third modification example. As can be seen by referring to FIG. 11, the target objects B11 to B13 and the target objects B21 to B23 are placed on shelves of a store E41. In addition, the arm apparatus 10 suspended from a ceiling surface is present in the store E41. Similarly to the example explained with reference to FIG. 6, the target objects B11 to B13 and the target objects B21 to B23 are not limited to fruits.

On the other hand, in the example depicted in FIG. 11, the freshness of the target object B11 associated with a relatively higher price (120 yen) has become lower than the freshness of the target object B12 associated with a relatively lower price (100 yen). The target object B11 having freshness that has become relatively lower should be associated with a price lower than that of the target object B12 having relatively higher freshness. It is supposed here that the freshness of the target object B11 has already been determined as described above. Then, it is supposed that the processing target, which has been the target object B11, is now the target object B12. Note that the order of freshness determination is not limited. For example, the freshness of the target object B12 may be determined earlier, and the processing target which has been the target object B12 may be now the target object B11.

The operation control section 213 controls the arm apparatus 10 such that the arm apparatus 10 reaches for the target object B12 at a predetermined timing. Similarly to the example explained with reference to FIG. 6, the predetermined timing is not limited.

Then, the acquiring section 211 acquires image data (first image data) obtained by the image sensor 112. The determining section 212 determines the type of the target object B12 on the basis of the image data. It is mainly supposed here that the amount of the reference gas to be sprayed onto the target object B12 is adjusted according to the type of the target object B12. However, similarly to the example explained with reference to FIG. 6, another parameter may change according to the type of the target object B12.

The operation control section 213 controls the nozzle 130 such that the reference gas is sprayed onto the target object B12. Then, the odor sensor 110 senses odor data of the target object B12. The acquiring section 211 acquires the odor data (first odor data) of the target object sensed by the odor sensor 110.

In addition, the determining section 212 determines the freshness (first freshness) of the target object B12 on the basis of the odor data. Then, the determining section 212 determines whether or not a relation between the freshness of the target object B11 and the target object B12 as examples of a plurality of target objects satisfies a predetermined condition. Here, the predetermined condition is not limited. For example, the determining section 212 determines whether or not a target object having relatively higher freshness is associated with a relatively higher price. In the example depicted in FIG. 11, the target object B12 having relatively higher freshness is associated with a relatively lower price (100 yen), and the target object B11 having relatively lower freshness is associated with a relatively higher price (120 yen).

The operation control section 213 controls a relation between the prices of the target object B11 and the target object B12 on the basis of the relation between the freshness of the target object B11 and the target object B12. More specifically, the operation control section 213 controls the relation between the prices of the target object B11, and the target object B12 such that either target object of the target object B11 and the target object B12 that has relatively higher freshness is associated with a relatively higher price. If the price of the target object B12 having relatively higher freshness is associated with a price higher than the price of the target object B11 having relatively lower freshness, the operation control section 213 controls the arm apparatus 10 such that the arm apparatus 10 reaches for the next target object without performing anything on the target object B12. Then, a similar process is executed also on the next target object.

On the other hand, as depicted in FIG. 11, in a case where the price of the target object B11 having relatively lower freshness is higher than the price of the target object B12 having relatively higher freshness, the operation control section 213 controls the arm apparatus 10 such that the target object B12 is gripped and lifted by the gripper 140. However, in a case where the robustness of the target object B12 against physical action is high, or in other similar cases, the target object B12 may be lifted from the beginning to measure the odor of the target object B12.

The operation control section 213 controls the nozzle 130 such that the reference gas is sprayed onto the target object B12 again. Then, the odor sensor 110 senses odor data (second odor data) of the target object B12 while the target object B12 is being gripped and lifted by the gripper 140. Then, the determining section 212 determines the freshness (second freshness) of the target object B12 on the basis of the odor data. Similarly, the determining section 212 determines whether or not a relation between the freshness of the target object B11 and the target object B12 satisfies a predetermined condition.

In a case where the relation between the freshness of the target object B11 and the target object B12 does not satisfy the predetermined condition, the operation control section 213 controls the arm apparatus 10 such that the arm apparatus 10 reaches for the next target object without performing anything on the target object B12. Then, a similar process is executed also on the next target object. On the other hand, in a case where the relation between the freshness of the target object B11 and the target object B12 satisfies the predetermined condition, the operation control section 213 performs control such that the predefined operation is executed. More specifically, in a case where the price of the target object B12 having relatively higher freshness is higher than the price of the target object B11 having relatively lower freshness, the operation control section 213 performs control such that the arrangement positions of the target object B11 and the target object B12 are switched.

Here, the switching of the arrangement positions of the target object B11 and the target object B12 may be realized in any manner. For example, the operation control section 213 may put the target object B12 aside at a predetermined waiting area, then move the target object B11 to a position where the target object B12 has been placed originally, and move the target object B12 to a position where the target object B11 has been placed originally. The waiting area may be present inside the arm apparatus 10 (e.g., a pocket, etc.) or may be present outside the arm apparatus 10 (e.g., a shelf, etc.).

As can be seen by referring to FIG. 11, a store E42 in a state after a lapse of time after the state of the store E41 is depicted. Here, because the price of the target object B12 having relatively higher freshness is higher than the price of the target object B11 having relatively lower freshness, the operation control section 213 performs control such that the arrangement positions of the target object B11 and the target object B12 are switched. Thereby, the target object B11 having relatively lower freshness becomes associated with a relatively lower price (100 yen), and the target object B12 having relatively higher freshness becomes associated with a relatively higher price (120 yen).

Note that the association of the price (100 yen) with the target object B11 and the association of the price (120 yen) with the target object B12 may be realized in any manner. For example, the operation control section 213 may control the arm apparatus 10 such that a price tag on which the price (100 yen) is written and a price tag on which the price (120 yen) is written are replaced with each other. Alternatively, the operation control section 213 may control the arm apparatus 10 such that the written price of the price tag associated with the target object B12 and the written price of the price tag associated with the target object B11 are changed.

In addition, FIG. 11 depicts an example of a process to be executed on the target objects B11 to B12. However, processes similar to the processes on the target objects B11 to B12 may be executed also on the other target objects (the target object B13, and the target objects B21 to B23).

Functional details of the system according to the third modification example have been explained thus far.

[2.4. Functional Details of System According to Fourth Modification Example]

Figure 12:
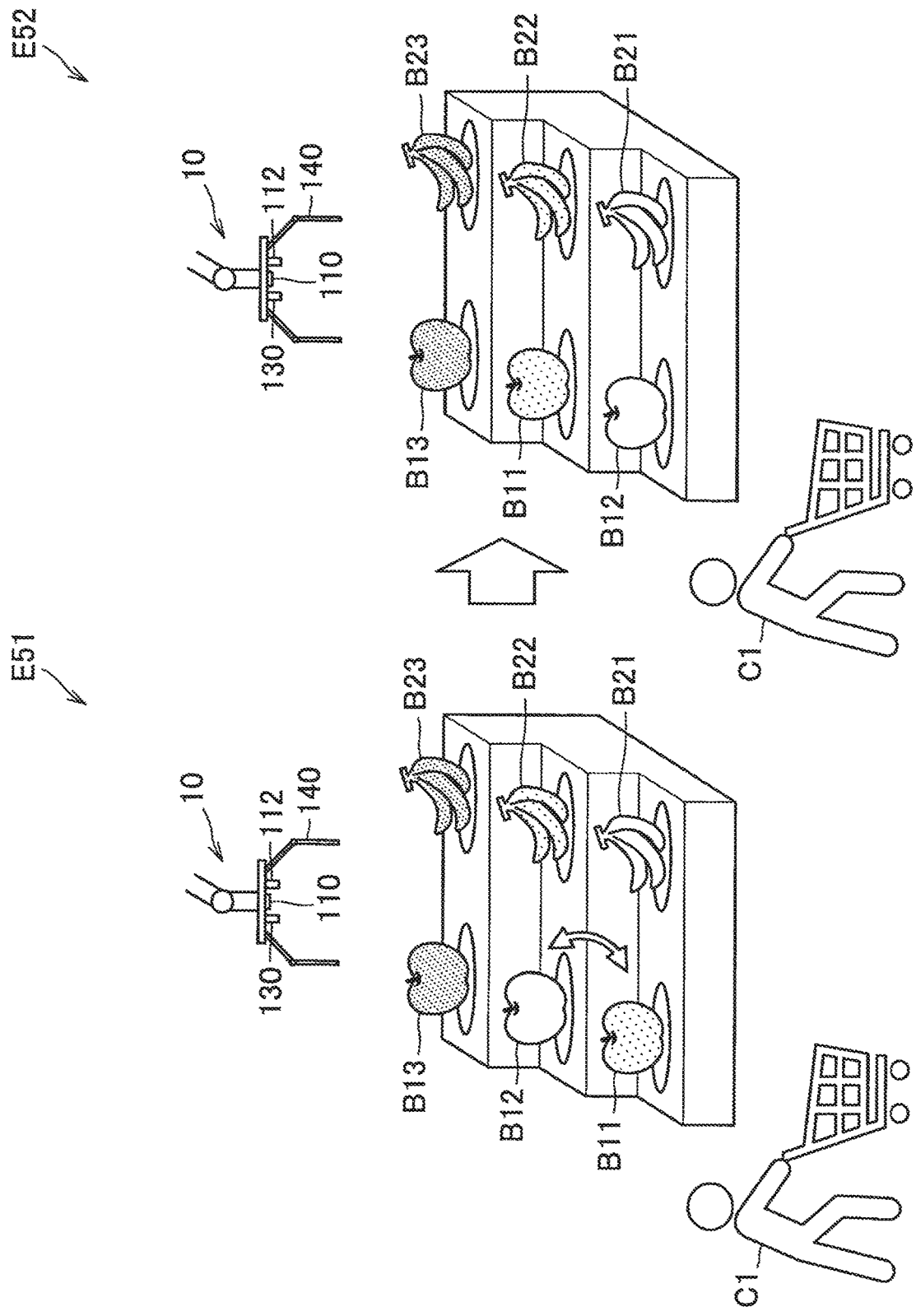
FIG. 12 is a figure for explaining functional details of a system according to a fourth modification example.

First, functional details of a system according to the fourth modification example are explained. FIG. 12 is a figure for explaining the functional details of the system according to the fourth modification example. As can be seen by referring to FIG. 12, the target objects B11 to B13 and the target objects B21 to B23 are placed on shelves of a store E51. In addition, the arm apparatus 10 suspended from a ceiling surface is present in the store E51. Similarly to the example explained with reference to FIG. 6, the target objects B11 to B13 and the target objects B21 to B23 are not limited to fruits.

On the other hand, in the example depicted in FIG. 12, the freshness of the target object B11 that is present at a position relatively closer to an aisle where a customer C1 passes through has become lower than the freshness of the target object B12 that is present at a position relatively farther from the aisle where the customer C1 passes through. In a case where it is considered that the higher the freshness of a target object is, the more prioritized the target object should be when target objects are to be used, the target object B11 having relatively lower freshness should be present at a position relatively farther from the aisle where the customer C1 passes through. It is supposed here that the freshness of the target object B11 has already been determined as described above. Then, it is supposed that the processing target which has been the target object B11 is now the target object B12. Note that the order of freshness determination is not limited. For example, the freshness of the target object B12 may be determined earlier, and the processing target which has been the target object B12 may be now the target object B11.

The operation control section 213 controls the arm apparatus 10 such that the arm apparatus 10 reaches for the target object B12 at a predetermined timing. Similarly to the example explained with reference to FIG. 6, the predetermined timing is not limited.

Then, the acquiring section 211 acquires image data (first image data) obtained by the image sensor 112. The determining section 212 determines the type of the target object B12 on the basis of the image data. It is mainly supposed here that the amount of the reference gas to be sprayed onto the target object B12 is adjusted according to the type of the target object B12. However, similarly to the example explained with reference to FIG. 6, another parameter may change according to the type of the target object B12.

The operation control section 213 controls the nozzle 130 such that the reference gas is sprayed onto the target object B12. Then, the odor sensor 110 senses odor data of the target object B12. The acquiring section 211 acquires the odor data (first odor data) of the target object sensed by the odor sensor 110.

In addition, the determining section 212 determines the freshness (first freshness) of the target object B12 on the basis of the odor data. Then, the determining section 212 determines whether or not a relation between the freshness of the target object B11 and the target object B12 as examples of a plurality of target objects satisfies a predetermined condition. Here, the predetermined condition is not limited. For example, the determining section 212 determines whether or not a target object having relatively lower freshness is present at a position relatively farther from the aisle where the customer C1 passes through. In the example depicted in FIG. 12, the target object B12 having relatively higher freshness is present at a position relatively farther from the aisle where the customer C1 passes through, and the target object B11 having relatively lower freshness is present at a position relatively closer to the aisle where the customer C1 passes through.

In a case where the target object B12 having relatively higher freshness is present at a position closer to the aisle where the customer C1 passes through than the target object B11 having relatively lower freshness is, the operation control section 213 control the arm apparatus 10 such that the arm apparatus 10 reaches for the next target object without performing anything on the target object B12. Then, a similar process is executed also on the next target object.

On the other hand, as depicted in FIG. 12, in a case where the target object B12 having relatively higher freshness is present at a position farther from the aisle where the customer C1 passes through than the target object B11 having relatively lower freshness is, the operation control section 213 controls the arm apparatus 10 such that the target object B12 is gripped and lifted by the gripper 140. However, in a case where the robustness of the target object B12 against physical action is high, or in other similar cases, the target object B12 may be lifted from the beginning to measure the odor of the target object B12.

The operation control section 213 controls the nozzle 130 such that the reference gas is sprayed onto the target object B12 again. Then, the odor sensor 110 senses odor data (second odor data) of the target object B12 while the target object B12 is being gripped and lifted by the gripper 140. Then, the determining section 212 determines the freshness (second freshness) of the target object B12 on the basis of the odor data. Similarly, the determining section 212 determines whether or not a relation between the freshness of the target object B11 and the target object B12 satisfies a predetermined condition.

In a case where the relation between the freshness of the target object B11 and the target object B12 does not satisfy the predetermined condition, the operation control section 213 controls the arm apparatus 10 such that the arm apparatus 10 reaches for the next target object without performing anything on the target object B12. Then, a similar process is executed also on the next target object. On the other hand, in a case where the relation between the freshness of the target object B11 and the target object B12 satisfies the predetermined condition, the operation control section 213 performs control such that the predefined operation is executed. More specifically, in a case where the target object B12 having relatively higher freshness is present at a position farther from the aisle where the customer C1 passes through than the target object B11 having relatively lower freshness is, the operation control section 213 performs control such that the arrangement positions of the target object B11 and the target object B12 are switched.

The switching of the arrangement positions of the target object B11 and the target object B12 may be realized in any manner, similarly to the example explained with reference to FIG. 11.

As can be seen by referring to FIG. 12, a store E52 in a state after a lapse of time after the state of the store E51 is depicted. Here, because the target object B12 having relatively higher freshness is present at a position farther from the aisle where the customer C1 passes through than the target object B12 having relatively lower freshness is, the operation control section 213 performs control such that the arrangement positions of the target object B11 and the target object B12 are switched. Thereby, the target object B11 having relatively lower freshness is now present at a position relatively farther from the aisle where the customer C1 passes through, and the target object B12 having relatively higher freshness is now present at a position relatively closer to the aisle where the customer C1 passes through.

Note that, in the example explained here, the operation control section 213 controls distances of the target object B11 and the target object B12 from the aisle where the customer C1 passes through, on the basis of a relation between the freshness of the target object B11 and the target object B12. However, distances between target objects, and the aisle where the customer C1 passes through are examples of use priorities. That is, the operation control section 213 may control a relation between the use priorities of the target object B11 and the target object B12 on the basis of a relation between the freshness of the target object B11 and the target object B12. More specifically, the operation control section 213 may control the relation between the use priorities of the target object B11 and the target object B12 such that either target object of the target object B11 and the target object B12 that has relatively higher freshness has a relatively higher use priority.

Alternatively, it can be considered in some cases that the lower the freshness of a target object is, the more prioritized the target object should be when target objects are to be used. In view of this, the operation control section 213 may control the relation between the use priorities of the target object B11 and the target object B12 such that either target object of the target object B11 and the target object B12 that has relatively lower freshness has a relatively higher use priority. For example, in a case where the target object B11 having relatively lower freshness is present at a position farther from the aisle where the customer C1 passes through than the target object B12 having relatively higher freshness is, the operation control section 213 may perform control such that the arrangement positions of the target object B11 and the target object B12 are switched.

In addition, FIG. 12 depicts an example of processes to be executed on the target objects B11 to B12. However, processes similar to the processes on the target objects B11 to B12 may be executed also on the other target objects (the target object B13, and the target objects B21 to B23).

Functional details of the system according to the fourth modification example have been explained thus far.

[2.5. Functional Details of System According to Fifth Modification Example]

Figure 13:
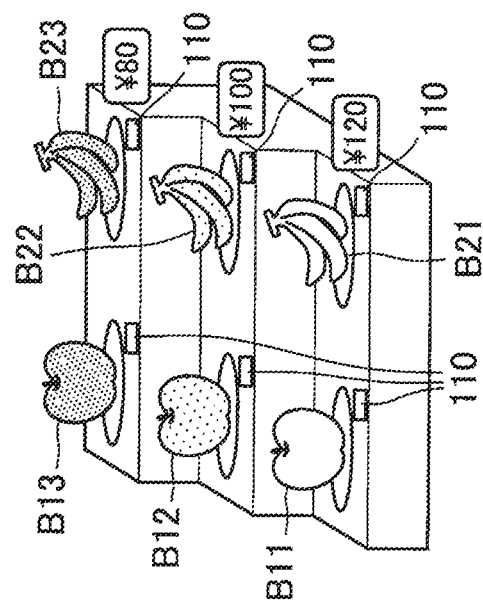
FIG. 13 is a figure for explaining functional details of a system according to a fifth modification example.

First, functional details of a system according to the fifth modification example are explained. FIG. 13 is a figure for explaining the functional details of the system according to the fifth modification example. As can be seen by referring to FIG. 13, the target objects B11 to B13 and the target objects B21 to B23 are placed on shelves of a store E61. Similarly to the example explained with reference to FIG. 6, the target objects B11 to B13 and the target objects B21 to B23 are not limited to fruits. In addition, the freshness and price of each of the target objects B11 to B13 and the target objects B21 to B22 are similar to those in the example explained with reference to FIG. 6.

As described above, the positions where the odor sensors 110 are provided are not limited. For example, the odor sensors 110 may be provided at positions (e.g., shelves, etc.) not on the arm apparatus 10. In the example depicted in FIG. 13, each odor sensor 110 is provided corresponding to one of the target objects B11 to B13 and the target objects B21 to B23. However, the positions where target objects are provided, and the number of the target objects provided are not limited. For example, one odor sensor 110 may be provided to a plurality of target objects. For example, one odor sensor 110 may be provided to the target object B11 and the target object B21, one odor sensor 110 may be provided to the target object B12 and the target object B22, and one odor sensor 110 may be provided to the target object B13 and the target object B23.

In addition, as described above, movement of each of the target objects B11 to B13 and the target objects B21 to B23 may be realized by a technique other than movement of the gripper 140. For example, movement of each of the target objects B11 to B13 and the target objects B21 to B23 may be realized by movement of a surface (e.g., a shelf, etc.) on which each of the target objects B11 to B13 and the target objects B21 to B23 is placed.

Functional details of the system according to the fifth modification example have been explained thus far.

3. CONCLUSION

According to the embodiment of the present disclosure, a control apparatus including a determining section that determines freshness of a target object on the basis of odor data of the target object sensed by an odor sensor and an operation control section that performs control such that operation predefined for the target object is executed on the basis of the freshness is provided.

Because the freshness of the target object is determined on the basis of the odor data of the target object according to the configuration, the freshness of the target object can be determined highly precisely even without applying physical action to the target object, as compared with a case that the freshness is determined by using image recognition. In addition, because the freshness of the target object is determined on the basis of the odor data of the target object according to the configuration, the freshness of the target object is determined more highly precisely as compared with a case that freshness recorded on an IC tag is read out, and a case that a bioelectrical impedance method is used. In addition, according to the configuration, it becomes possible to reduce labor costs (e.g., labor costs required for food displays, or food management, etc.) by executing operation suited for the target object automatically.

While a suitable embodiment of the present disclosure has been explained in detail with reference to the attached figures thus far, the technical scope of the present disclosure is not limited to the example. It is obvious that it is possible for those with ordinary knowledge in the technical field of the present disclosure to conceive of various types of altered example or corrected example within the scope of the technical idea described in claims, and those various types of altered example or corrected example are understood to belong to the technical scope of the present disclosure certainly.

For example, it is mainly explained in the description above that the amount of the reference gas to be sprayed onto target objects is adjusted according to the type of the target object. However, if the density of target objects is recognized from image data, the amount of the reference gas to be sprayed onto the target objects may be adjusted according to the density of the target objects. Alternatively, thresholds to be compared with freshness may change according to the density of the target objects. Alternatively, a correspondence between odor data and the freshness may change according to the density of the target objects.

In addition, a plurality of target objects may be arranged in any manner. For example, a plurality of target objects may be put next to each other without partitions therebetween as depicted in FIG. 6, or may be put next to each other with partitions partitioning them. In addition, a plurality of target objects may be put next to each other with spaces therebetween as depicted in FIG. 6, or may be put next to each other with overlaps therebetween. Alternatively, a plurality of target objects may be stacked one on another to form piles of them. At this time, in a case a target object that should be disposed is found in the plurality of stacked target objects, the operation control section 213 may control the arm apparatus 10 such that the stacked target objects are moved one by one, and the target object that should be disposed is dug out, and moved to a space where disposed articles are placed.

The individual examples described above can be combined as appropriate. For example, the operation control section 213 may control the arm apparatus 10 such that a target object is moved to a space where disposed articles are placed in a case where the freshness of the target object is lower than a first threshold, and may control the arm apparatus 10 such that a target object is moved to a space associated with a price of the target object in a case where the freshness of the target object is higher than the first threshold, and the price is lower than a price-related second threshold. That is, the operation control section 213 can select a space to which a target object should be moved, according to the freshness of the target object.

In addition, the advantages described in the present specification are presented merely for explanation or illustration but not for limitation. That is, the technology according to the present disclosure can exhibit other advantages that are obvious for those skilled in the art from the description of this specification, along with the advantages described above, or instead of the advantages described above.

Note that configurations like the ones mentioned below also belong to the technical scope of the present disclosure.

(1)

A control apparatus including:

a determining section that determines freshness of a target object on the basis of odor data of the target object sensed by an odor sensor; and an operation control section that performs control such that operation predefined for the target object is executed on the basis of the freshness.

(2)

The control apparatus according to (1), in which the operation control section performs control such that a gas is sprayed onto the target object before the odor sensor senses the odor data.

(3)

The control apparatus according to (2), in which the operation control section adjusts an amount of the gas according to a type of the target object.

(4)

The control apparatus according to any one of (1) to (3), in which the odor sensor is provided on an inner side of a gripper, and the gripper is provided with a blocking member that blocks an air inflow from an outer side of the gripper to the inner side.

(5)

The control apparatus according to any one of (1) to (3), in which the odor sensor is provided on an inner side of a gripper, and a shape of the gripper changes into a shape that blocks an air inflow from an outer side of the gripper to the inner side when the gripper grips the target object.

(6)

The control apparatus according to any one of (1) to (3), in which the operation control section performs control such that the target object is gripped and lifted by a gripper on the basis of first freshness satisfying a predetermined condition, the first freshness being based on first odor data of the target object, and performs control such that the operation is executed on the basis of second freshness satisfying the predetermined condition, the second freshness being based on second odor data of the target object sensed while the target object is being gripped and lifted by the gripper.

(7)

The control apparatus according to any one of (1) to (6), in which the operation control section performs control such that the target object is moved on the basis of the freshness.

(8)

The control apparatus according to (7), in which the operation control section moves the target object to a predetermined space in a case where the freshness is higher than a threshold.

(9)

The control apparatus according to (7), in which the operation control section moves the target object to a predetermined space in a case where the freshness is lower than a threshold.

(10)

The control apparatus according to (8) or (9), in which the predetermined space is a space where a disposed article is placed.

(11)

The control apparatus according to (8) or (9), in which the predetermined space is a space associated with a predetermined price.

(12)

The control apparatus according to any one of (1) to (6), in which the operation control section performs control such that a price according to the freshness is associated with the target object.

(13)

The control apparatus according to any one of (1) to (6), in which the operation control section performs control such that a use priority according to the freshness is associated with the target object.

(14)

The control apparatus according to any one of (1) to (6), in which the operation control section controls a relation between use priorities of a plurality of target objects on the basis of a relation between freshness of the plurality of target objects.

(15)

The control apparatus according to (14), in which the operation control section controls the relation between the use priorities of the plurality of target objects such that target objects with relatively higher freshness in the plurality of target objects have relatively higher use priorities.

(16)

The control apparatus according to (14), in which the operation control section controls the relation between the use priorities of the plurality of target objects such that target objects with relatively lower freshness in the plurality of target objects have relatively higher use priorities.

(17)

The control apparatus according to any one of (1) to (6), in which the operation control section controls a relation between prices of a plurality of target objects on the basis of a relation between freshness of the plurality of target objects.

(18)

The control apparatus according to (17), in which the operation control section controls the relation between the prices of the plurality of target objects such that prices of target objects with relatively higher freshness in the plurality of target objects have relatively higher prices.

(19)

A control method including:

determining freshness of a target object on the basis of odor data of the target object sensed by an odor sensor; and performing, by a processor, control such that operation predefined for the target object is executed on the basis of the freshness.

(20)

A program for causing a computer to function as a control apparatus including:

a determining section that determines freshness of a target object on the basis of odor data of the target object sensed by an odor sensor; and an operation control section that performs control such that operation predefined for the target object is executed on the basis of the freshness.

REFERENCE SIGNS LIST

1: System
10: Arm apparatus
110: Odor sensor
112: Image sensor
120: Joint section
130: Nozzle
140: Gripper
141: Finger
142: Blocking member
171: Air-feeding apparatus
172: Reference gas
180: Air-feeding tube
20: Control apparatus
210: Control section
211: Acquiring section
212: Determining section
213: Operation control section
230: Storage section
51: Disposed-article space

The invention claimed is:

1. A control apparatus, comprising:
at least one processor configured to:
control a spray of a gas onto a target object;
adjust an amount of the spray of the gas based on a type of the target object;
acquire first odor data of the target object, wherein the first odor data is sensed by an odor sensor subsequent to the spray of the gas;
determine first freshness of the target object based on the first odor data of the target object; and
execute a specific operation for the target object based on the first freshness.

2. The control apparatus according to claim 1, wherein the odor sensor is on an inner side of a gripper, and
the gripper includes a blocking member that blocks an air inflow from an outer side of the gripper to the inner side.

3. The control apparatus according to claim 1, wherein the odor sensor is on an inner side of a gripper, and
a first shape of the gripper changes into a second shape that blocks an air inflow from an outer side of the gripper to the inner side in a case where the gripper grips the target object.

4. The control apparatus according to claim 1, wherein the at least one processor is further configured to:
control, based on the first freshness, a gripper to grip and lift the target object, wherein the first freshness satisfies a specific condition;
acquire second odor data of the target object, wherein the second odor data is sensed by the odor sensor in a state where the target object is gripped and lifted by the gripper;
determine second freshness of the target object based on the second odor data, wherein the second freshness satisfies the specific condition; and
execute the specific operation based on the second freshness.

5. The control apparatus according to claim 1, wherein the at least one processor is further configured to control, based on the first freshness, a movement of the target object.

6. The control apparatus according to claim 5, wherein the at least one processor is further configured to move the target object to a specific space based on a value of the first freshness that is higher than a threshold value.

7. The control apparatus according to claim 5, wherein the at least one processor is further configured to move the target object to a specific space based on a value of the first freshness that is lower than a threshold value.

8. The control apparatus according to claim 7, wherein the specific space is for placement of a disposed article.

9. The control apparatus according to claim 6, wherein the specific space is associated with a specific price.

10. The control apparatus according to claim 1, wherein the at least one processor is further configured to control an association of a price of the target object with the first freshness of the target object.

11. The control apparatus according to claim 1, wherein the at least one processor is further configured to control an association of a use priority of the target object with the first freshness of the target object.

12. The control apparatus according to claim 1, wherein
the at least one processor is further configured to control
a first relation between use priorities of a plurality of target objects based on a second relation between freshness of the plurality of target objects, and
the plurality of target objects includes the target object.

13. The control apparatus according to claim 12, wherein the at least one processor is further configured to control the first relation between the use priorities of the plurality of target objects such that at least one target object of the plurality of target objects with higher freshness than remaining target objects of the plurality of target objects has a higher use priority than the remaining target objects.

14. The control apparatus according to claim 12, wherein the at least one processor is further configured to control the first relation between the use priorities of the plurality of target objects such that at least one target object of the plurality of target objects with lower freshness than remaining target objects of the plurality of target objects has a higher use priority than the remaining target objects.

15. The control apparatus according to claim 1, wherein
the at least one processor is further configured to control
a first relation between prices of a plurality of target objects based on a second relation between freshness of the plurality of target objects, and
the plurality of target objects includes the target object.

16. The control apparatus according to claim 15, wherein the at least one processor is further configured to control the first relation between the prices of the plurality of target objects such that at least one target object of the plurality of target objects with higher freshness than remaining target objects of the plurality of target objects has a higher price than the remaining target objects.

17. A control method, comprising:
controlling, by at least one processor, a spray of a gas onto a target object;
adjusting, by the at least one processor, an amount of the spray of the gas based on a type of the target object;
acquiring, by the at least one processor, odor data of the target object, wherein the odor data is sensed by an odor sensor subsequent to the spray of the gas;
determining, by the at least one processor, freshness of the target object based on the odor data of the target object; and
executing, by the at least one processor, a specific operation for the target object based on the freshness.

18. A non-transitory computer-readable medium having stored thereon, computer-executable instructions which, when executed by a computer, cause the computer to execute operations, the operations comprising:

controlling a spray of a gas onto a target object;
adjusting an amount of the spray of the gas based on a type of the target object;
acquiring odor data of the target object, wherein the odor data is sensed by an odor sensor subsequent to the spray of the gas;
determining freshness of the target object based on the odor data of the target object; and
executing a specific operation for the target object based on the freshness.

* * * * *